United States Patent
Owen et al.

(10) Patent No.: US 10,426,167 B2
(45) Date of Patent: *Oct. 1, 2019

(54) SYNERGISTIC FUNGICIDAL MIXTURES AND COMPOSITIONS COMPRISING 5-FLUORO-4-IMINO-3-METHYL-1-TOSYL-3,4-DIHYDROPYRIMIDIN-2(1H)-ONE FOR FUNGAL CONTROL

(71) Applicant: Adama Makhteshim Ltd., Beer Sheva (IL)

(72) Inventors: W. John Owen, Carmel, IN (US); Chenglin Yao, Carmel, IN (US); Beth Lorsbach, Indianapolis, IN (US)

(73) Assignee: ADAMA MAKHTESHIM LTD., Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/022,027

(22) Filed: Jun. 28, 2018

(65) Prior Publication Data

US 2018/0303096 A1    Oct. 25, 2018

Related U.S. Application Data

(63) Continuation of application No. 15/377,859, filed on Dec. 13, 2016, now Pat. No. 10,051,862, which is a continuation of application No. 14/585,962, filed on Dec. 30, 2014, now Pat. No. 9,538,753.

(60) Provisional application No. 61/922,616, filed on Dec. 31, 2013, provisional application No. 61/922,630, filed on Dec. 31, 2013, provisional application No. 61/922,640, filed on Dec. 31, 2013.

(51) Int. Cl.

| | |
|---|---|
| A61K 31/513 | (2006.01) |
| C07D 239/47 | (2006.01) |
| A01N 43/54 | (2006.01) |
| A01N 37/34 | (2006.01) |
| A01N 37/50 | (2006.01) |
| A01N 43/40 | (2006.01) |
| A01N 43/56 | (2006.01) |
| A01N 43/88 | (2006.01) |
| A01N 47/08 | (2006.01) |
| A01N 43/653 | (2006.01) |
| A01N 45/02 | (2006.01) |
| A01N 47/04 | (2006.01) |
| A01N 47/14 | (2006.01) |
| A01N 47/24 | (2006.01) |

(52) U.S. Cl.
CPC ............ *A01N 43/54* (2013.01); *A01N 37/34* (2013.01); *A01N 37/50* (2013.01); *A01N 43/40* (2013.01); *A01N 43/56* (2013.01); *A01N 43/653* (2013.01); *A01N 43/88* (2013.01); *A01N 45/02* (2013.01); *A01N 47/04* (2013.01); *A01N 47/08* (2013.01); *A01N 47/14* (2013.01); *A01N 47/24* (2013.01)

(58) Field of Classification Search
CPC ............................ A61K 31/513; C07D 239/47
USPC ........................................ 514/274; 544/326
See application file for complete search history.

(56) References Cited

U.S. PATENT DOCUMENTS

| | | |
|---|---|---|
| 3,309,359 A | 3/1967 | Duschinsky et al. |
| 3,368,938 A | 2/1968 | Berger et al. |
| 3,635,977 A | 1/1972 | Lutz et al. |
| 3,868,373 A | 2/1975 | Hoffer |
| 4,009,272 A | 2/1977 | Konig et al. |
| 4,845,081 A | 7/1989 | Sloan |
| 4,996,208 A | 2/1991 | Lindner et al. |
| 5,962,489 A | 10/1999 | Mueller et al. |
| 6,066,638 A | 5/2000 | Bereznak et al. |
| 6,617,330 B2 | 9/2003 | Walter |
| 7,914,799 B2 | 3/2011 | Jira et al. |
| 8,263,603 B2 | 9/2012 | Boebel et al. |
| 8,318,758 B2 | 11/2012 | Boebel et al. |
| 8,470,839 B2 | 6/2013 | Boebel et al. |
| 8,552,020 B2 | 10/2013 | Pobanz et al. |
| 8,658,660 B2 | 2/2014 | Boebel et al. |
| 8,916,579 B2 | 12/2014 | Boebel et al. |

(Continued)

FOREIGN PATENT DOCUMENTS

| | | |
|---|---|---|
| CN | 102548980 | 7/2012 |
| CN | 102574831 | 7/2012 |

(Continued)

OTHER PUBLICATIONS

Jan. 5, 2018 Response to Oct. 5, 2017 Non-Final Office Action issued by the U.S. Patent and Trademark Office in connection with U.S. Appl. No. 15/377,854.

(Continued)

*Primary Examiner* — Douglas M Willis
(74) *Attorney, Agent, or Firm* — Gary J. Gershik; Cooper & Dunham LLP

(57) ABSTRACT

A fungicidal composition containing a fungicidally effective amount of the compound of Formula I:

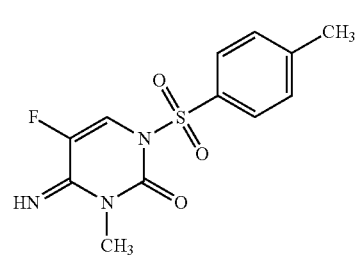

Formula I 5-fluoro-4-imino-3-methyl-1-tosyl-3,4-dihydropyrimidin-2(1H)-one, and at least one fungicide to provide synergistic control of selected fungi wherein the at least one fungicide is a multi-site inhibitor or a strobilurin inhibitor.

20 Claims, No Drawings

(56) References Cited

U.S. PATENT DOCUMENTS

| | | |
|---|---|---|
| 9,000,002 B2 | 4/2015 | Pobanz et al. |
| 9,006,259 B2 | 4/2015 | Webster et al. |
| 9,271,497 B2 | 3/2016 | Lorsbach et al. |
| 9,321,734 B2 | 4/2016 | Lorsbach et al. |
| 9,526,245 B2 | 12/2016 | Owen et al. |
| 9,532,570 B2 | 1/2017 | Owen et al. |
| 9,538,753 B2 | 1/2017 | Owen et al. |
| 9,622,474 B2 | 4/2017 | Lorsbach et al. |
| 9,642,368 B2 | 5/2017 | Lorsbach et al. |
| 9,840,475 B2 | 12/2017 | Lorsbach et al. |
| 9,840,476 B2 | 12/2017 | Choy et al. |
| 9,850,215 B2 | 12/2017 | Choy et al. |
| 9,862,686 B2 | 1/2018 | Boebel et al. |
| 9,908,855 B2 | 3/2018 | Lorsbach et al. |
| 10,045,533 B2 | 8/2018 | Owen et al. |
| 10,045,534 B2 | 8/2018 | Owen et al. |
| 10,051,862 B2 | 8/2018 | Owen et al. |
| 10,059,703 B2 | 8/2018 | Lorsbach et al. |
| 2003/0039667 A1 | 2/2003 | Jira et al. |
| 2008/0004253 A1 | 1/2008 | Branstetter et al. |
| 2008/0234295 A1 | 9/2008 | Beck et al. |
| 2008/0269238 A1 | 10/2008 | Sugihara et al. |
| 2009/0203647 A1 | 8/2009 | Benko et al. |
| 2010/0022538 A1 | 1/2010 | Boebel et al. |
| 2010/0029482 A1 | 2/2010 | Benko et al. |
| 2010/0029483 A1 | 2/2010 | Iskandar et al. |
| 2011/0034490 A1 | 2/2011 | Boebel et al. |
| 2011/0034491 A1 | 2/2011 | Boebel et al. |
| 2011/0034492 A1 | 2/2011 | Boebel et al. |
| 2011/0034493 A1 | 2/2011 | Boebel et al. |
| 2011/0053891 A1 | 3/2011 | Boebel et al. |
| 2011/0082162 A1 | 4/2011 | Lorsbach et al. |
| 2011/0263627 A1 | 10/2011 | Boebel et al. |
| 2012/0088665 A1 | 4/2012 | Dietz et al. |
| 2013/0045984 A1 | 2/2013 | Boebel et al. |
| 2014/0011824 A1 | 1/2014 | Pobanz et al. |
| 2015/0111851 A1 | 4/2015 | Boebel et al. |
| 2015/0181874 A1 | 7/2015 | Owen et al. |
| 2015/0181875 A1 | 7/2015 | Owen et al. |
| 2015/0181883 A1 | 7/2015 | Owen et al. |
| 2015/0183749 A1 | 7/2015 | Choy et al. |
| 2015/0183750 A1 | 7/2015 | Choy et al. |
| 2015/0191436 A1 | 7/2015 | Webster et al. |
| 2015/0342188 A1 | 12/2015 | Lorsbach et al. |
| 2015/0353506 A1 | 12/2015 | Lorsbach et al. |
| 2015/0359225 A1 | 12/2015 | Lorsbach et al. |
| 2016/0192653 A1 | 7/2016 | Lorsbach et al. |
| 2016/0198711 A1 | 7/2016 | Lorsbach et al. |
| 2016/0280662 A1 | 9/2016 | Choy et al. |
| 2016/0280663 A1 | 9/2016 | Choy et al. |
| 2017/0008855 A1 | 1/2017 | Boebel et al. |
| 2017/0086458 A1 | 3/2017 | Owen et al. |
| 2017/0086459 A1 | 3/2017 | Owen et al. |
| 2017/0204069 A1 | 7/2017 | Lorsbach et al. |
| 2017/0240540 A1 | 8/2017 | Lorsbach et al. |
| 2018/0000082 A1 | 1/2018 | Klittich et al. |
| 2018/0072686 A1 | 3/2018 | Choy et al. |
| 2018/0303094 A1 | 10/2018 | Owen et al. |
| 2018/0303095 A1 | 10/2018 | Owen et al. |

FOREIGN PATENT DOCUMENTS

| | | |
|---|---|---|
| EP | 0102908 | 3/1984 |
| EP | 0139613 | 5/1985 |
| EP | 0253714 | 1/1988 |
| EP | 0332579 | 9/1989 |
| EP | 0877022 | 4/2003 |
| EP | 1952689 | 8/2008 |
| GB | 1461184 | 1/1977 |
| JP | 6001793 | 1/1994 |
| JP | 2002-530409 | 9/2002 |
| JP | 2012-502905 | 2/2012 |
| JP | 2013-501728 | 1/2013 |
| JP | 6128658 | 5/2017 |
| NZ | 597644 | 9/2014 |
| WO | WO 97/33890 A1 | 9/1997 |
| WO | WO 02/30922 A2 | 4/2002 |
| WO | WO 2008/083465 A1 | 7/2008 |
| WO | WO 2009/063075 A2 | 5/2009 |
| WO | WO 2009/094442 A2 | 7/2009 |
| WO | WO 2010/047866 A2 | 4/2010 |
| WO | WO 2010/085377 A2 | 7/2010 |
| WO | WO 2010/139653 | 12/2010 |
| WO | WO 2011/017538 A1 | 2/2011 |
| WO | WO 2011/017540 A1 | 2/2011 |
| WO | WO 2011/017544 A1 | 2/2011 |
| WO | WO 2011/017545 A1 | 2/2011 |
| WO | WO 2011/017547 A1 | 2/2011 |
| WO | WO 2011/043876 A1 | 4/2011 |
| WO | WO 2011/044213 | 4/2011 |
| WO | WO 2011/137002 A1 | 11/2011 |
| WO | WO 2013/025795 A1 | 2/2013 |
| WO | WO 2014/105821 A1 | 7/2014 |
| WO | WO 2014/105841 A1 | 7/2014 |
| WO | WO 2014/105844 A1 | 7/2014 |
| WO | WO 2014/105845 A1 | 7/2014 |
| WO | WO 2015/103142 A1 | 7/2015 |
| WO | WO 2015/103144 A1 | 7/2015 |
| WO | WO 2015/103259 A1 | 7/2015 |
| WO | WO 2015/103261 A1 | 7/2015 |
| WO | WO 2015/103262 A1 | 7/2015 |
| WO | WO 2016/106138 | 6/2016 |

OTHER PUBLICATIONS

Jan. 26, 2018 Final Office Action issued by the U.S. Patent and Trademark Office in connection with U.S. Appl. No. 15/377,854.

Jan. 5, 2018 Response to Oct. 5, 2017 Non-Final Office Action issued by the U.S. Patent and Trademark Office in connection with U.S. Appl. No. 15/377,845.

Jan. 26, 2018 Final Office Action issued by the U.S. Patent and Trademark Office in connection with U.S. Appl. No. 15/377,845.

Feb. 8, 2018 Non-Final Office Action issued by the U.S. Patent and Trademark Office in connection with U.S. Appl. No. 15/813,562.

Feb. 20, 2018 Opposition issued by the Costa Rican Patent Office against Costa Rican Patent Application No. 2017-0325.

Mar. 15, 2018 Office Action issued by the Cuban Patent Office in connection with Cuban Patent Application No. 2016-0100 (including English language translation).

Mar. 15, 2018 Office Action issued by the Cuban Patent Office in connection with Cuban Patent Application No. 2016-0102 (including English language translation).

PCT International Search Report dated Feb. 25, 2016 in connection with PCT International Application No. PCT/US2015/066756 (WO 2016/106138), filed Dec. 18, 2015.

International Preliminary Report on Patentability dated Jun. 27, 2017 in connection with PCT International Application No. PCT/US2015/066756 (WO 2016/106138), filed Dec. 18, 2015.

Written Opinion of the International Searching Authority dated Feb. 25, 2016 in connection with PCT International Application No. PCT/US2015/066756 (WO 2016/106138), filed Dec. 18, 2015.

Aug. 14, 2017 Response to Mar. 15, 2017 Non-Final Office Action issued by the U.S. Patent and Trademark Office in connection with U.S. Appl. No. 15/173,493.

Aug. 15, 2017 Response to Mar. 20, 2017 Office Action issued by the U.S. Patent and Trademark Office in connection with U.S. Appl. No. 15/173,529.

Oct. 5, 2017 Non-Final Office Action issued by the U.S. Patent and Trademark Office in connection with U.S. Appl. No. 15/377,854.

Oct. 5, 2017 Non-Final Office Action issued by the U.S. Patent and Trademark Office in connection with U.S. Appl. No. 15/377,845.

Aug. 28, 2014 First Examination Report issued by the Australian Patent Office in connection with Australian Patent Application No. 2011245544.

Jul. 29, 2016 Response to Jul. 1, 2016 Office Action issued by the Brazilian Patent Office in connection with Brazilian Patent Application No. BR112012027439-2.

Jul. 11, 2017 Response to Jan. 11, 2017 Office Action issued by the Canadian Patent Office in connection with Canadian Patent Application No. 2,797,226.

(56) References Cited

OTHER PUBLICATIONS

Sep. 28, 2017 Office Action issued by the Canadian Patent Office in connection with Canadian Patent Application No. 2,797,226.
Oct. 3, 2017 Office Action issued by the Costa Rican Patent Office in connection with Costa Rican Patent Application No. 2012-0584 (including English language translation).
Nov. 20, 2017 Response to Oct. 3, 2017 Office Action issued by the Costa Rican Patent Office in connection with Costa Rican Patent Application No. 2012-0584.
Mar. 22, 2017 Notice of Preliminary Rejection issued by Korean Patent Office in connection with Korean Patent Application No. 10-2012-7030690.
May 22, 2017 Response to Mar. 22, 2017 Notice of Preliminary Rejection issued by Korean Patent Office in connection with Korean Patent Application No. 10-2012-7030690.
Jun. 21, 2017 Communication pursuant to Rule 164(1) EPC and Partial Supplementary European Search Report issued by the European Patent Office in connection with European Patent Application No. 14877285.8.
Aug. 16, 2017 Response to Jun. 21, 2017 Communication and Partial Supplementary European Search Report pursuant to Rule 164(1) EPC issued by the European Patent Office in connection with European Patent Application No. 14877285.8.
Sep. 13, 2017 Supplementary European Search Report issued by the European Patent Office in connection with European Patent Application No. 14877285.8.
Sep. 29, 2017 Communication pursuant to Rules 70(2) and 70a(2) issued by the European Patent Office in connection with European Patent Application No. 14877285.8.
May 15, 2017 Office Action issued by the Eurasian Patent Office in connection with Eurasian Patent Application No. 201691353 (including English language translation).
Sep. 15, 2017 Response to May 15, 2017 Office Action issued by the Eurasian Patent Office in connection with Eurasian Patent Application No. 201691353.
Sep. 27, 2017 Response to Dec. 23, 2016 First Examination Report issued by the Australian Patent Office in connection with Australian Patent Application No. 2014373959.
Jul. 28, 2017 First Substantive Report issued by the Chilean Patent Office in connection with Chilean Patent Application No. 2016-001677.
Oct. 26, 2017 Response to Jul. 28, 2017 First Substantive Report issued by the Chilean Patent Office in connection with Chilean Patent Application No. 2016-001677.
Jul. 12, 2017 Response to Jan. 12, 2017 First Examination Report issued by the New Zealand Patent Office in connection with New Zealand Application No. 722439.
Aug. 9, 2017 Further Examination Report issued by the New Zealand Patent Office in connection with New Zealand Patent Application No. 722439.
Nov. 9, 2017 Response to Aug. 9, 2017 Further Examination Report issued by the New Zealand Patent Office in connection with New Zealand Patent Application No. 722439.
Nov. 20, 2017 Further Examination Report issued by the New Zealand Patent Office in connection with New Zealand Patent Application No. 722439.
Apr. 10, 2017 Office Action issued by the Panamanian Patent Office in connection with Panamanian Patent Application No. 91211 (including English language translation).
Jul. 24, 2017 Technical Examination Report issued by the Salvadorian Patent Office in connection with Salvadorian Patent Application No. 20160020316 (including English language translation).
Nov. 23, 2017 Response to Jul. 24, 2017 Technical Examination Report issued by the Salvadorian Patent Office in connection with Salvadorian Patent Application No. 20160020316.
Jun. 13, 2017 Communication pursuant to Rule 164(1) EPC and Partial Supplementary European Search Report issued by the European Patent Office in connection with European Patent Application No. 14875976.4.

Sep. 15, 2017 European Supplementary Search Report issued by the European Patent Office in connection with European Patent Application No. 14875976.4.
Oct. 4, 2017 Communication pursuant to Rules 70(2) and 70a(2) issued by the European Patent Office in connection with European Patent Application No. 14875976.4.
Jun. 14, 2017 Office Action issued by the Eurasian Patent Office in connection with Eurasian Patent Application No. 201691351 (including English language translation).
Oct. 16, 2017 Response to Jun. 14, 2017 Office Action issued by the Eurasian Patent Office in connection with Eurasian Patent Application No. 201691351.
Sep. 27, 2017 Response to Dec. 23, 2016 First Examination Report issued by the Australian Patent Office in connection with Australian Patent Application No. 2014373961.
Jul. 12, 2017 Response to Jan. 12, 2017 First Examination Report issued by the New Zealand Patent Office in connection with New Zealand Patent Application No. 722438.
Aug. 9, 2017 Further Examination Report issued by the New Zealand Patent Office in connection with New Zealand Patent Application No. 722438.
Nov. 17, 2017 Post-Acceptance Voluntary Amendment filed in Response to Aug. 9, 2017 Further Examination Report issued by the New Zealand Patent Office in connection with New Zealand Patent Application No. 722438.
May 9, 2017 Response to Nov. 15, 2016 Communication pursuant to Rule 161(2) and 162 issued by the European Patent Office in Connection with European Patent Application No. 14877100.9.
Oct. 2, 2017 Supplementary European Search Report issued by the European Patent Office in connection with European Patent Application No. 14877100.9.
Oct. 19, 2017 Communication pursuant to Rules 70(2) and 70a(2) EPC issued by the European Patent Office in connection with European Patent Application No. 14877100.9.
Jun. 19, 2017 Response to Feb. 22, 2017 Office Action issued by the Eurasian Patent Office in connection with Eurasian Patent Application No. 201691346.
Aug. 14, 2017 Response to Nov. 14, 2016 First Examination Report issued by the Australian Patent Office in connection with Australian Patent Application No. 2014373850.
Sep. 1, 2017 Second Examination Report issued by the Australian Patent Office in connection with Australian Patent Application No. 2014373850.
Nov. 3, 2017 Response to Sep. 1, 2017 Second Examination Report issued by the Australian Patent Office in connection with Australian Patent Application No. 2014373850.
Aug. 3, 2017 Opposition issued by the Costa Rican Patent Office against Costa Rican Patent Application No. 2016-0000345 (including English language translation).
Sep. 12, 2017 Response to Aug. 3, 2017 Opposition issued by the Costa Rican Patent Office against Costa Rican Patent Application No. 2016-0000345.
Jun. 6, 2017 Response to Notice Before Examination issued by the Israeli Patent Office in Connection with Israeli Patent Application No. 246461.
Jul. 10, 2017 Response to Jan. 10, 2017 First Examination Report issued by the New Zealand Patent Office in connection with New Zealand Patent Application No. 722419.
Aug. 9, 2017 Further Examination Report issued by the New Zealand Patent Office in connection with New Zealand Patent Application No. 722419.
Oct. 23, 2017 Response to Aug. 9, 2017 Further Examination Report issued by the New Zealand Patent Office in connection with New Zealand Patent Application No. 722419.
Apr. 5, 2017 Office Action issued by the Panamanian Patent Office in connection with Panamanian Patent Application No. 91208 (including English Language translation).
Jul. 20, 2017 Technical Examination Report issued by the Salvadorian Patent Office in connection with Salvadorian Patent Application No. 20160020321 (including English language translation).
Nov. 23, 2017 Response to Jul. 20, 2017 Technical Examination Report issued by the Salvadorian Patent Office in connection with Salvadorian Patent Application No. 20160020321.

(56) References Cited

OTHER PUBLICATIONS

Apr. 26, 2017 Response to Oct. 28, 2016 Communication pursuant to Rules 161(2) and 162 issued by the European Patent Office in connection with European Patent Application No. 14876883.1.
Aug. 4, 2017 Supplementary European Search Report issued by the European Patent Office in connection with European Patent Application No. 14876883.1.
Aug. 22, 2017 Communication pursuant to Rules 70(2) and 70a(2) issued by the European Patent Office in connection with European Patent Application No. 14876883.1.
Jun. 19, 2017 Response to Feb. 21, 2017 Office Action issued by the Eurasian Patent Office in connection with Eurasian Patent Application No. 201691345.
Aug. 14, 2017 Response to Nov. 14, 2016 First Examination Report issued by the Australian Patent Office in connection with Australian Patent Application No. 2014373852.
Sep. 1, 2017 Second Examination Report issued by the Australian Patent Office in connection with Australian Patent Application No. 2014373852.
Nov. 3, 2017 Response to Sep. 1, 2017 Second Examination Report issued by the Australian Patent Office in connection with Australian Patent Application No. 2014373852.
Jun. 16, 2017 Opposition issued by Costa Rican Patent Office in connection with Costa Rican Patent Application No. 2016-0342 (inlcuding English language translation).
Jul. 17, 2017 Response to Opposition filed by Costa Rican Patent Office in connection with Costa Rican Patent Application No. 2016-0342.
Jun. 6, 2017 Response to Notice Before Examination issued by the Israeli Patent Office in Connection with Israeli Patent Application No. 246462.
Jul. 10, 2017 Response to Jan. 10, 2017 First Examination Report issued by the New Zealand Patent Office in connection with New Zealand Patent Application No. 722418.
Aug. 4, 2017 Further Examination Report issued by the New Zealand Patent Office in connection with New Zealand Patent Application No. 722418.
Oct. 20, 2017 Response to Aug. 4, 2017 Further Examination Report issued by the New Zealand Patent Office in connection with New Zealand Patent Application No. 722418.
Apr. 5, 2017 Office Action issued by the Panamanian Patent Office in connection with Panamanian Patent Application No. 91209 (including English language translation).
Jul. 28, 2017 Technical Report issued by the Salvadorian Patent Office in connection with Salvadorian Patent Application No. 20160020322 (including English language translation).
May 17, 2017 Response to Nov. 18, 2016 Communication pursuant to Rules 161(2) and 162 issued by the European Patent Office in connection with European Patent Application No. 14876118.2.
Sep. 29, 2017 Supplementary European Search Report issued by the European Patent Office in connection with European Patent Application No. 14876118.2.
Oct. 17, 2017 Communication pursuant to Rules 70(2) and 70a(2) EPC issued by the European Patent Office in connection with European Patent Application No. 14876118.2.
Jun. 19, 2017 Response to Feb. 20, 2017 Office Action in connection with Eurasian Patent Application No. 201691344.
Aug. 14, 2017 Response to Nov. 14, 2016 First Examination Report issued by the Australian Patent Office in connection with Australian Patent Application No. 2014373853.
Sep. 1, 2017 Second Examination Report issued by the Australian Patent Office in connection with Australian Patent Application No. 2014373853.
Nov. 3, 2017 Response to Sep. 1, 2017 Second Examination Report issued by the Australian Patent Office in connection with Australian Patent Application No. 2014373853.
Jun. 16, 2017 Opposition issued by Costa Rican Patent Office in connection with Costa Rican Patent Application No. 2016-0344 (including English language translation).
Jul. 17, 2017 Response to Opposition filed by Costa Rican Patent Office in Connection with Costa Rican Patent Application No. 2016-0344.
Jun. 6, 2017 Response to Notice Before Examination issued by the Israeli Patent Office in connection with Israeli Patent No. 246470.
Jul. 10, 2017 Response to Jan. 10, 2017 First Examination Report issued by the New Zealand Patent Office in connection with New Zealand Patent Application No. 722436.
Aug. 9, 2017 Further Examination Report issued by the New Zealand Patent Office in connection with New Zealand Patent Application No. 722436.
Nov. 9, 2017 Response to Aug. 9, 2017 Further Examination Report issued by the New Zealand Patent Office in connection with New Zealand Patent Application No. 722436.
Apr. 7, 2017 Office Action issued by the Panamanian Patent Office in connection with Panamanian Patent Application No. 91210 (including English language translation).
Jul. 27, 2017 Technical Examination Report issued by Salvadorian Patent Office in connection with Salvadorian Patent Application No. 20160020320 (including English language translation).
Nov. 23, 2017 Response to Jul. 27, 2017 Technical Examination Report issued by Salvadorian Patent Office in connection with Salvadorian Patent Application No. 20160020320.
Aug. 16, 2017 Response to Office Action issued by the Thai Patent Office in connection with Thai Patent Application No. 1601003884.
Aug. 4, 2017 Office Action issued by the Colombian Patent Office in connection with Colombian Patent Application No. NC2017/0007059 (including English language translation).
Oct. 4, 2017 Response to Aug. 4, 2017 Office Action issued by the Colombian Patent Office in connection with Colombian Patent Application No. NC2017/0007059.
Birari et al. (2009) "Synthesis of Cytosine Derivatives and Study of their Alkylation Under Mild Conditions," Organic Preparations and Procedures International: The New Journal for Organic Synthesis, 41(6):515-532.
FRAC Code List: Fungicide sorted by mode of action, (Dec. 31, 2009), pp. 1-10, available at http://www.frac.info/frac/publication/anhangFRAC_Code_List_2010.pdf.
J. Rheinheimer Ed.-Kramer W. et al. (2008) "Succinate Dehydrogenase Inhibitors," Modern Crop Protection Compounds, Wiley-VCH, pp. 496-505.
Kuck et al. (2007) "Sterol Biosynthesis Inhibitors," Modern Crop Protection Compounds, Wiley-VCH, pp. 605-650.
Sauter (2007) "Strobilurins and Other Complex III Inhibitors," Modern Crop Protection Compounds, Wiley-VCH, pp. 457-495.
Sierotzki H. et al. (2013) "A Review of Current Knowledge of Resistance Aspects for the Next-Generation Succinate Dehydrogenase Inhibitor Fungicides," Phytopathology, American Phytopathological Society, 103:880-887.
Dec. 12, 2017 Response to Nov. 20, 2017 Further Examination Report issued by the New Zealand Patent Office in connection with New Zealand Patent Application No. 722439.
Dec. 22, 2017 Response to Apr. 10, 2017 Office Action issued by the Panamanian Patent Office in connection with Panamanian Patent Application No. 91211.
Dec. 22, 2017 Response to Apr. 5, 2017 Office Action issued by the Panamanian Patent Office in connection with Panamanian Patent Application No. 91208.
Dec. 22, 2017 Response to Apr. 5, 2017 Office Action issued by the Panamanian Patent Office in connection with Panamanian Patent Application No. 91209.
Dec. 22, 2017 Response to Apr. 7, 2017 Office Action issued by the Panamanian Patent Office in connection with Panamanian Patent Application No. 91210.
PCT International Search Report dated Sep. 21, 2010 in connection with PCT/US2010/044579 (WO 2011/017540), filed Aug. 5, 2010.
PCT International Search Report dated Sep. 21, 2010 in connection with PCT/US2010/044592 (WO 2011/017547), filed Aug. 5, 2010.
PCT International Search Report dated Sep. 23, 2010 in connection with PCT/US2010/044576 (WO 2011/017538), filed Aug. 5, 2010.
PCT International Search Report dated Jul. 5, 2011 in connection with PCT/US2011/033203 (WO 2011/137002), filed Apr. 20, 2011.

(56) References Cited

OTHER PUBLICATIONS

Written Opinion of the International Searching Authority dated Jul. 5, 2011 in connection with PCT/US2011/033203 (WO 2011/137002), filed Apr. 20, 2011.
International Preliminary Report on Patentability dated Oct. 30, 2012 in connection with PCT/US2011/033203 (WO 2011/137002), filed Apr. 20, 2011.
PCT International Search Report dated Oct. 15, 2012 in connection with PCT/US2012/050930 (WO 2013/025795), filed Aug. 15, 2012.
Written Opinion of the International Searching Authority dated Oct. 15, 2012 in connection with PCT/US2012/050930 (WO 2013/025795), filed Aug. 15, 2012.
International Preliminary Report on Patentability dated Feb. 18, 2014 in connection with PCT/US2012/050930 (WO 2013/025795), filed Aug. 15, 2012.
PCT International Search Report dated Apr. 8, 2015 in connection with PCT/US2014/072566 (WO 2015/103142), filed Dec. 29, 2014.
International Preliminary Report on Patentability dated Jul. 5, 2016 in connection with PCT/US2014/072566 (WO 2015/103142), filed Dec. 29, 2014.
Written Opinion of the International Searching Authority dated Apr. 8, 2015 in connection with PCT/US2014/072566 (WO 2015/103142), filed Dec. 29, 2014.
PCT International Search Report dated Apr. 2, 2015 in connection with PCT/US2014/072569 (WO 2015/103144), filed Dec. 29, 2014.
International Preliminary Report on Patentability dated Jul. 5, 2016 in connection with PCT/US2014/072569 (WO 2015/103144), filed Dec. 29, 2014.
Written Opinion of the International Searching Authority dated Apr. 2, 2015 in connection with PCT/US2014/072569 (WO 2015/103144), filed Dec. 29, 2014.
PCT International Search Report dated Apr. 28, 2015 in connection with PCT/US2014/072745 (WO 2015/103259), filed Dec. 30, 2014.
International Preliminary Report on Patentability dated Jul. 5, 2016 in connection with PCT/US2014/072745 (WO 2015/103259), filed Dec. 30, 2014.
Written Opinion of the International Searching Authority dated Apr. 28, 2015 in connection with PCT/US2014/072745 (WO 2015/103259), filed Dec. 30, 2014.
PCT International Search Report dated Apr. 29, 2015 in connection with PCT/US2014/072747 (WO 2015/103261), filed Dec. 30, 2014.
International Preliminary Report on Patentability dated Jul. 5, 2016 in connection with PCT/US2014/072747 (WO 2015/103261), filed Dec. 30, 2014.
Written Opinion of the International Searching Authority dated Apr. 29, 2015 in connection with PCT/US2014/072747 (WO 2015/103261), filed Dec. 30, 2014.
PCT International Search Report dated May 21, 2015 in connection with PCT/US2014/072748 (WO 2015/103262), filed Dec. 30, 2014.
International Preliminary Report on Patentability dated Jul. 5, 2016 in connection with PCT/US2014/072748 (WO 2015/103262), filed Dec. 30, 2014.
Written Opinion of the International Searching Authority dated May 21, 2015 in connection with PCT/US2014/072748 (WO 2015/103262), filed Dec. 30, 2014.
PCT International Search Report dated Sep. 30, 2009 in connection with PCT/US/2009/031683 (WO 2009/094442), filed Jan. 22, 2009.
PCT International Search Report dated Mar. 14, 2011 in connection with PCT/US/2011/020351 (WO 2011/085084), filed Jan. 6, 2011.
PCT International Search Report dated Oct. 1, 2010 in connection with PCT/US/2010/044588 (WO 2011/017545), filed Aug. 5, 2010.
PCT International Search Report dated Oct. 9, 2012 in connection with PCT/US/2012/050931 (WO 2013/025796), filed Aug. 15, 2012.
PCT International Search Report dated Apr. 22, 2011 in connection with PCT/US/2010/060792 (WO 2011/084611), filed Dec. 16, 2010.
Nov. 10, 2011 Non-Final Office Action issued by the U.S. Patent and Trademark Office in connection with U.S. Appl. No. 13/090,616.
Feb. 9, 2012 Response to Nov. 10, 2011 Non-Final Office Action issued by the U.S. Patent and Trademark Office in connection with U.S. Appl. No. 13/090,616.
May 14, 2013 Non-Final Office Action issued by the U.S. Patent and Trademark Office in connection with U.S. Appl. No. 13/586,450.
Aug. 14, 2013 Response to May 14, 2013 Non-Final Office Action issued by the U.S. Patent and Trademark Office in connection with U.S. Appl. No. 13/586,450.
Mar. 4, 2015 Non-Final Office Action issued by the U.S. Patent and Trademark Office in connection with U.S. Appl. No. 14/584,347.
Jun. 4, 2015 Response to Mar. 4, 2015 Non-Final Office Action issued by the U.S. Patent and Trademark Office in connection with U.S. Appl. No. 14/584,347.
Jul. 2, 2015 Final Office Action issued by the U.S. Patent and Trademark Office in connection with U.S. Appl. No. 14/584,347.
Sep. 2, 2015 Response to Jul. 2, 2015 Final Office Action issued by the U.S. Patent and Trademark Office in connection with U.S. Appl. No. 14/584,347.
Sep. 9, 2015 Advisory Action issued by the U.S. Patent and Trademark Office in connection with U.S. Appl. No. 14/584,347.
Nov. 23, 2016 Non-Final Office Action issued by the U.S. Patent and Trademark Office in connection with U.S. Appl. No. 15/173,493.
Mar. 1, 2017 Response to Nov. 23, 2016 Non-Final Office Action issued by the U.S. Patent and Trademark Office in connection with U.S. Appl. No. 15/173,493.
Mar. 15, 2017 Final Office Action issued by the U.S. Patent and Trademark Office in connection with U.S. Appl. No. 15/173,493.
Mar. 5, 2015 Non-Final Office Action issued by the U.S. Patent and Trademark Office in connection with U.S. Appl. No. 14/584,368.
Jun. 4, 2015 Response to Mar. 5, 2015 Non-Final Office Action issued by the U.S. Patent and Trademark Office in connection with U.S. Appl. No. 14/584,368.
Jul. 2, 2015 Final Office Action issued by the U.S. Patent and Trademark Office in connection with U.S. Appl. No. 14/584,368.
Sep. 2, 2015 Response to Jul. 2, 2015 Final Office Action issued by the U.S. Patent and Trademark Office in connection with U.S. Appl. No. 14/584,368.
Sep. 10, 2015 Advisory Action issued by the U.S. Patent and Trademark Office in connection with U.S. Appl. No. 14/584,368.
Dec. 1, 2016 Non-Final Office Action issued by the U.S. Patent and Trademark Office in connection with U.S. Appl. No. 15/173,529.
Mar. 1, 2017 Response to Dec. 1, 2016 Non-Final Office Action issued by the U.S. Patent and Trademark Office in connection with U.S. Appl. No. 15/173,529.
Dec. 18, 2015 Non-Final Office Action issued by the U.S. Patent and Trademark Office in connection with U.S. Appl. No. 14/585,945.
Mar. 16, 2016 Response to Dec. 18, 2015 Non-Final Office Action issued by the U.S. Patent and Trademark Office in connection with U.S. Appl. No. 14/585,945.
Apr. 11, 2016 Final Office Action issued by the U.S. Patent and Trademark Office in connection with U.S. Appl. No. 14/585,945.
Aug. 11, 2016 Response to Apr. 11, 2016 Final Office Action issued by the U.S. Patent and Trademark Office in connection with U.S. Appl. No. 14/585,945.
Dec. 18, 2015 Non-Final Office Action issued by the U.S. Patent and Trademark Office in connection with U.S. Appl. No. 14/585,952.
Mar. 16, 2016 Response to Dec. 18, 2015 Non-Final Office Action issued by the U.S. Patent and Trademark Office in connection with U.S. Appl. No. 14/585,952.
Apr. 12, 2016 Final Office Action issued by the U.S. Patent and Trademark Office in connection with U.S. Appl. No. 14/585,952.
Aug. 11, 2016 Response to Apr. 12, 2016 Final Office Action issued by the U.S. Patent and Trademark Office in connection with U.S. Appl. No. 14/585,952.
Dec. 18, 2015 Non-Final Office Action issued by the U.S. Patent and Trademark Office in connection with U.S. Appl. No. 14/585,962.
Mar. 16, 2016 Response to Dec. 18, 2015 Non-Final Office Action issued by the U.S. Patent and Trademark Office in connection with U.S. Appl. No. 14/585,962.
Apr. 12, 2016 Final Office Action issued by the U.S. Patent and Trademark Office in connection with U.S. Appl. No. 14/585,962.

(56) References Cited

OTHER PUBLICATIONS

Aug. 12, 2016 Response to Apr. 12, 2016 Final Office Action issued by the U.S. Patent and Trademark Office in connection with U.S. Appl. No. 14/585,962.
Mar. 20, 2017 Office Action issued by the U.S. Patent and Trademark Office in connection with U.S. Appl. No. 15/173,529.
Dec. 7, 2012 Supplemental European Search Report issued by the EPO in connection with European Patent Application No. 10807172.1, filed Aug. 5, 2010.
Jun. 24, 2013 Supplemental European Search Report issued by the EPO in connection with European Patent Application No. 11775446.5, filed Apr. 20, 2011.
Sep. 25, 2014 Communication pursuant to Article 94(3) EPC issued by the European Patent Office in connection with European Patent Application No. 11775446.5.
Feb. 4, 2015 Response to Sep. 25, 2014 Communication pursuant to Article 94(3) EPC issued by the European Patent Office in connection with European Patent Application No. 11775446.5.
European Search Opinion issued by the EPO in connection with European Patent Application No. 11775446.5.
Feb. 3, 2014 Response to European Search Opinion issued by the EPO in connection with European Patent Application No. 11775446.5.
Mar. 23, 2015 Response to Aug. 28, 2014 First Examination Report issued by the Australian Patent Office in connection with Australian Patent Application No. 2011245544.
Jan. 11, 2017 Office Action issued by the Canadian Patent Office in connection with Canadian Patent Application No. 2,797,226.
Aug. 25, 2015 Office Action issued by the Chilean Patent Office in connection with Chilean Patent Application No. 2979-2012.
May 26, 2016 Office Action issued by the Chilean Patent Office in connection with Chilean Patent Application No. 2979-2012.
Aug. 22, 2016 Response to May 26, 2016 Office Action issued by the Chilean Patent Office in connection with Chilean Patent Application No. 2979-2012.
Oct. 17, 2013 Office Action issued by the Chinese Patent Office in connection with Chinese Patent Application No. 201180031680.8.
Feb. 28, 2014 Response to Oct. 17, 2013 Office Action issued by the Chinese Patent Office in connection with Chinese Patent Application No. 201180031680.8.
May 23, 2014 Office Action issued by the Chinese Patent Office in connection with Chinese Patent Application No. 201180031680.8.
Sep. 24, 2013 Office Action issued by the Colombian Patent Office in connection with Colombian Patent Application No. 12213540.
Dec. 18, 2013 Response to Sep. 24, 2013 Office Action issued by the Colombian Patent Office in connection with Colombian Patent Application No. 12213540.
Jun. 22, 2015 Response to Mar. 22, 2015 Office Action issued by the Israeli Patent Office in connection with Israeli Patent Application No. 222646.
Feb. 10, 2015 Office Action issued by the Japanese Patent Office in connection with Japanese Patent Application No. 2013-508042.
May 10, 2015 Response to Feb. 10, 2015 Office Action issued by the Japanese Patent Office in connection with Japanese Patent Application No. 2013-508042.
Jul. 3, 2014 Response to May 26, 2014 Office Action issued by the Mexican Patent Office Mexican Patent Application No. MX/a/2012/012530.
Jun. 14, 2013 First Examination Report issued by the New Zealand Patent Office in connection with New Zealand Patent Application No. 603151.
Oct. 1, 2013 Response to Jun. 14, 2013 First Examination Report issued by the New Zealand Patent Office in connection with New Zealand Patent Application No. 603151.
Jun. 17, 2016 Office Action issued by the Filipino Patent Office in connection with Filipino Patent Application No. 1/2012/502138.
Sep. 28, 2016 Office Action issued by the Filipino Patent Office in connection with Filipino Patent Application No. 1/2012/502138.
Jan. 19, 2015 Office Action issued by the Russian Patent Office in connection with Russian Patent Application No. 2012150293.
Apr. 19, 2015 Response to Jan. 19, 2015 Office Action issued by the Russian Patent Office in connection with Russian Patent Application No. 2012150293.
Apr. 16, 2014 Office Action issued by the Ukrainian Patent Office in connection with Ukrainian Patent Application No. 2012 13412.
Oct. 30, 2014 Response to Apr. 16, 2014 Office Action issued by the Ukrainian Patent Office in connection with Ukrainian Patent Application No. 2012 13412.
Oct. 5, 2016 Communication pursuant to Rules 161(2) and 162 EPC issued by the European Patent Office in connection with European Patent Application No. 14877285.8.
Dec. 23, 2016 First Examination Report issued by the Australian Patent Office in connection with Australian Patent Application No. 2014373959.
Aug. 9, 2016 Office Action issued by the Colombian Patent Office in connection with Colombian Patent Application No. NC2016-0000512.
Jul. 14, 2016 Office Action issued by the Cuban Patent Office in connection with Cuban Patent Application No. 2016-0099.
Oct. 6, 2016 Response to Jul. 14, 2016 Office Action issued by the Cuban Patent Office in connection with Cuban Patent Application No. 2016-0099.
Nov. 20, 2016 Response to Jul. 20, 2016 Notice Before Examination issued by the Israeli Patent Office in connection with Israeli Patent Application No. 246511.
Jan. 12, 2017 First Examination Report issued by the New Zealand Patent Office in connection with New Zealand Patent Application No. 722439.
Oct. 5, 2016 Communication pursuant to Rules 161(2) and 162 EPC issued by the European Patent Office in connection with European Patent Application No. 14875976.4.
Dec. 23, 2016 First Examination Report issued by the Australian Patent Office in connection with Australian Patent Application No. 2014373961.
Nov. 20, 2016 Response to Jul. 20, 2016 Notice Before Examination issued by the Israeli Patent Office in connection with Israeli Patent Application No. 246512.
Jan. 12, 2017 First Examination Report issued by the New Zealand Patent Office in connection with New Zealand Patent Application No. 722438.
Nov. 15, 2016 Communication pursuant to Rules 161(2) and 162 issued by the European Patent Office in connection with European Patent Application No. 14877100.9.
Feb. 22, 2017 Office Action issued by the Eurasian Patent Office in connection with Eurasian Patent Application No. 201691346.
Nov. 14, 2016 First Patent Examination Report issued by the Australian Patent Office in connection with Australian Patent Application No. 2014373850.
Sep. 14, 2016 Office Action issued by the Colombian Patent Office in connection with Colombian Patent Application No. NC2016-0000472.
Nov. 28, 2016 Response to Sep. 14, 2016 Office Action issued by the Colombian Patent Office in connection with Colombian Patent Application No. NC2016-0000472.
Nov. 1, 2016 Notice issued by the Costa Rican Patent Office in connection with Costa Rican Patent Application No. 2016-0000345.
Jan. 11, 2017 Response to Nov. 1, 2016 Notice issued by the Costa Rican Patent Office in connection with Costa Rican Patent Application No. 2016-0000345.
Jul. 19, 2016 Office Action issued by the Cuban Patent Office in connection with Cuban Patent Application No. 2016-0100.
Oct. 6, 2016 Response to Jul. 19, 2016 Office Action issued by the Cuban Patent Office in connection with Cuban Patent Application No. 2016-0100.
Jan. 10, 2017 First Examination Report issued by the New Zealand Patent Office in connection with New Zealand Patent Application No. 722419.
Aug. 25, 2016 Office Action issued by the Vietnamese Patent Office in connection with Vietnamese Patent Application No. 1-2016-02805.
Sep. 23, 2016 Response to Aug. 25, 2016 Office Action issued by the Vietnamese Patent Office in connection with Vietnamese Patent Application No. 1-2016-02805.

(56) References Cited

OTHER PUBLICATIONS

Oct. 28, 2016 Communication pursuant to Rules 161(2) and 162 issued by the European Patent Office in connection with European Patent Application No. 14876883.1.
Feb. 21, 2017 Office Action issued by the Eurasian Patent Office in connection with Eurasian Patent Application No. 201691345.
Nov. 14, 2016 First Patent Examination Report issued by the Australian Patent Office in connection with Australian Patent Application No. 2014373852.
Sep. 21, 2016 Office Action issued by the Colombian Patent Office in connection with Colombian Patent Application No. NC2016-0000502.
Nov. 28, 2016 Response to Sep. 21, 2016 Office Action issued by the Colombian Patent Office in connection with Colombian Patent Application No. NC2016-0000502.
Jul. 19, 2016 Office Action issued by the Cuban Patent Office in connection with Cuban Patent Application No. 2016-0103.
Oct. 11, 2016 Response to Jul. 19, 2016 Office Action issued by the Cuban Patent Office in connection with Cuban Patent Application No. 2016-0103.
Jan. 10, 2017 First Examination Report issued by the New Zealand Patent Office in connection with New Zealand Patent Application No. 722418.
Aug. 25, 2016 Office Action issued by the Vietnamese Patent Office in connection with Vietnamese Patent Application No. 1-2016-02806.
Sep. 23, 2016 Response to Aug. 25, 2016 Office Action issued by the Vietnamese Patent Office in connection with Vietnamese Patent Application No. 1-2016-02806.
Nov. 18, 2016 Communication pursuant to Rules 161(2) and 162 issued by the European Patent Office in connection with European Patent Application No. 14876118.2.
Feb. 20, 2017 Office Action issued by the Eurasian Patent Office in connection with Eurasian Patent Application No. 201691344.
Nov. 14, 2016 First Patent Examination Report issued by the Australian Patent Office in connection with Australian Patent Application No. 2014373853.
Sep. 21, 2016 Office Action issued by the Colombian Patent Office in connection with Colombian Patent Application No. NC2016-0000520.
Jul. 19, 2016 Office Action issued by the Cuban Patent Office in connection with Cuban Patent Application No. 2016-0102.
Oct. 6, 2016 Response to Jul. 19, 2016 Office Action issued by the Cuban Patent Office in connection with Cuban Patent Application No. 2016-0102.
Aug. 25, 2016 Office Action issued by the Vietnamese Patent Office in connection with Vietnamese Patent Application No. 1-2016-02807.
Sep. 23, 2016 Response to Aug. 25, 2016 Office Action issued by the Vietnamese Patent Office in connection with Vietnamese Patent Application No. 1-2016-02807.
Feb. 28, 2017 Response to Sep. 21, 2016 Office Action issued by the Colombian Patent Office in connection with Colombian Patent Application No. NC2016-0000520.
Jan. 10, 2017 First Examination Report issued by the New Zealand Patent Office in connection with New Zealand Patent Application No. 722436.
Bera et al. (2002) "Nucleosides with furanyl scaffolds." Tetrahedron, Elsevier Science Publishers. 58(24): 4865-4871.
Chiacchio et al. (2003) "Enantioselective Syntheses and Cytotoxicity of N,O-Nucleosides." J. of Medicinal Chemistry, American Chemical Society. 46(1): 3696-3702.
Duschinsky et al. (1966) "Nucleosides. XXXIII. N4-Acylated 5-Fluorocytosines and a Direct Synthesis of 5-Fluoro-2'-deoxycytidine" J. of Medicinal Chemistry. 9(4): 566-572.
Duschinsky et al. (1964) "Cytosine derivatives." CAPLUS Abstract 61:18527.
Gabriella et al. (1963) "Some 5-fluorosulfanilamidopyrimidines." Gazzette Chimica Italiana. 93(10): 1268-1278.

Jaworski et al. (1990) "Infrared spectra and tautomerism of 5-fluorocytosine, 5-bromocytosine and 5-iodocytosine Matrix isolation and theoretical ab initio studies." J. of Molecular Structure. 223: 63-92.
Kulikowski et al. (1978) "Methylation and tautomerism of 5-fluorocytosine nucleosides and their analogues." J. Nucleic Acids Research, Special Publication. 4(1): S7-S10.
Lewis et al. (1995) "Synthesis and in vitro anti-human cytomegalovirus (hcmv) activity of certain alkenyl substituted cytosines and 5-halocytosines." J. of Heterocyclic Chemistry. 32(5): 1513-1515.
Liang et al. (2007) "A facile synthesis and herbicidal activities of novel fluorine-containing thiazolo[4,5-d] pyrimidin-7(6H)-ones." J. of Fluorine Chemistry, 128(7): 879-884.
Robins et al. (1972) "A direct synthesis of 5-fluorocytosine and its nucleosides using trifluromethyl hypofluorite." J. of the Chemical Society, Chemical Communications. 1(1):18.
Waring (2009) "Defining optimum lipophilicity and molecular weight ranges for drug candidates—Molecular weight dependent lower logD limits based on permeability." Bioorganic & Medicinal Chemistry Letters, 19(10): 2844-2851.
Woese et al, (1990) "Towards a natural system of organisms: Proposal for the domains Archaea, Bacteria, and Eucarya." Proc. Acad. Sci., 87:4576-4579.
Zhang et al. (1989) "Improved method for synthesis of 5-fluorocytosine (5-FC)." CAPLUS Abstract, 111:134074.
May 8, 2018 Response to Feb. 8, 2018 Non-Final Office Action issued by the U.S. Patent and Trademark Office in connection with U.S. Appl. No. 15/813,562.
Jun. 8, 2018 Final Office Action issued by the U.S. Patent and Trademark Office in connection with U.S. Appl. No. 15/813,562.
Oct. 5, 2017 Non-Final Office Action issued by the U.S. Patent and Trademark Office in connection with U.S. Appl. No. 15/377,859.
Jan. 5, 2018 Response to Oct. 5, 2017 Non-Final Office Action issued by the U.S. Patent and Trademark Office in connection with U.S. Appl. No. 15/377,859.
Jan. 25, 2018 Final Office Action issued by the U.S. Patent and Trademark Office in connection with U.S. Appl. No. 15/377,859.
Mar. 26, 2018 Response to Jan. 26, 2018 Final Office Action issued by the U.S. Patent and Trademark Office in connection with U.S. Appl. No. 15/377,845.
Mar. 26, 2018 Response to Jan. 26, 2018 Final Office Action issued by the U.S. Patent and Trademark Office in connection with U.S. Appl. No. 15/377,854.
Mar. 26, 2018 Response to Jan. 25, 2018 Final Office Action issued by the U.S. Patent and Trademark Office in connection with U.S. Appl. No. 15/377,859.
Mar. 28, 2018 Response to Sep. 28, 2017 Office Action issued by the Canadian Patent Office in connection with Canadian Patent Application No. 2,797,226.
Aug. 7, 2014 Response to May 23, 2014 Office Action issued by the Chinese Patent Office in connection with Chinese Patent Application No. 201180031680.8.
Jan. 28, 2018 Office Action issued by the Costa Rican Patent Office in connection with Costa Rican Patent Application No. 2012-0584 (English language translation).
Mar. 6, 2018 Response to Jan. 28, 2018 Office Action issued by the Costa Rican Patent Office in connection with Costa Rican Patent Application No. 2012-0584.
May 3, 2018 Final Technical Report issued by the Costa Rican Patent Office in connection with Costa Rican Patent Application No. 2012-0584.
Aug. 14, 2018 Decision of Rejection issued by the Costa Rican Patent Office in connection with Costa Rican Patent Application No. 2012-0584.
Aug. 28, 2018 Notice of Appeal filed in response to Aug. 14, 2018 Decision of Rejection issued by the Costa Rican Patent Office in connection with Costa Rican Patent Application No. 2012-0584.
Feb. 19, 2018 Response to Jan. 5, 2018 Office Action issued by the Indonesian Patent Office in connection with Indonesian Patent No. W-00 2012 004824 (English language translation).
Nov. 30, 2017 Office Action issued by the Indian Patent Office in connection with Indian Patent Application No. 10041/DELNP/2012 (English language translation).

(56) References Cited

OTHER PUBLICATIONS

Mar. 22, 2018 Response to Nov. 30, 2017 Office Action issued by the Indian Patent Office in connection with Indian Patent Application No. 10041/DELNP/2012 (English language translation).
Mar. 27, 2018 Office Action issued by the Indian Patent Office in connection with Indian Patent Application No. 10041/DELNP/2012 (English language translation).
May 30, 2018 Response to Mar. 27, 2018 Office Action issued by the Indian Patent Office in connection with Indian Patent Application No. 10041/DELNP/2012 (English language translation).
Jun. 22, 2018 Hearing Notice for Aug. 23, 2018 Hearing issued by the Indian Patent Office in connection with Indian Patent Application No. 10041/DELNP/2012 (English language translation).
Sep. 6, 2018 Response to Aug. 23, 2018 Hearing conducted by the Indian Patent Office in connection with Indian Patent Application No. 10041/DELNP/2012 (English language translation).
Mar. 28, 2018 Response to Sep. 13, 2017 Supplementary European Search Report issued by the European Patent Office in connection with European Patent Application No. 14877285.8.
Sep. 21, 2018 Response to May 22, 2018 Communication pursuant to Article 94(3) issued by the European Patent Office in connection with European Patent Application No. 14877285.8.
Dec. 22, 2017 Office Action issued by the Eurasian Patent Office in connection with Eurasian Patent Application No. 201691353 (including English language translation).
Apr. 23, 2018 Response to Dec. 22, 2017 Office Action issued by the Eurasian Patent Office in connection with Eurasian Patent Application No. 201691353.
Jul. 11, 2018 Office Action issued by the Eurasian Patent Office in connection with Eurasian Patent Application No. 201691353 (including English language translation).
Dec. 19, 2017 Second Substantive Report issued by the Chilean Patent Office in connection with Chilean Patent Application No. 2016-001677.
Mar. 15, 2018 Response to Dec. 19, 2017 Second Substantive Report issued by the Chilean Patent Office in connection with Chilean Patent Application No. 2016-001677.
Apr. 4, 2018 Office Action issued by the Chinese Patent Office in connection with Chinese Patent Application No. 201480076563.7 (English language translation).
Aug. 20, 2018 Response to Apr. 4, 2018 Office Action issued by the Chinese Patent Office in connection with Chinese Patent Application No. 201480076563.7.
Feb. 20, 2018 Office Action issued by the Colombian Patent Office in connection with Colombian Patent Application No. NC2016-0000512.
Mar. 20, 2018 Response to Feb. 20, 2018 Office Action issued by the Colombian Patent Office in connection with Colombian Patent Application No. NC2016-0000512.
Aug. 16, 2018 Office Action issued by the Cuban Patent Office in connection with Cuban Patent Application No. 2016-0099 (including English language translation).
Aug. 28, 2018 Office Action issued by the Japanese Patent Office in connection with Japanese Patent Application No. 2016-543746.
Jul. 9, 2018 Response to Jun. 8, 2018 Office Action issued by the Mexican Patent Office in connection with Mexican Patent Application No. MX/a/2016/008758.
Dec. 12, 2017 Technical Examination Report issued by the Salvadorian Patent Office in connection with Salvadorian Patent Application No. 20160020316 (including English language translation).
Jul. 31, 2018 Office Action issued by the Taiwanese Patent Office in connection with Taiwanese Patent Application No. 103146555.
Apr. 13, 2018 Response to Sep. 15, 2017 European Supplementary Search Report issued by the European Patent Office in connection with European Patent Application No. 14875976.4.
May 22, 2018 Communication pursuant to Article 94(3) EPC issued by the European Patent Office in connection with European Patent Application No. 14875976.4.
Sep. 21, 2018 Response to May 22, 2018 Communication pursuant to Article 94(3) EPC issued by the European Patent Office in connection with European Patent Application No. 14875976.4.
Jan. 26, 2018 Office Action issued by the Eurasian Patent Office in connection with Eurasian Patent Application No. 201691351 (including English language translation).
May 28, 2018 Response to Jan. 26, 2018 Office Action issued by the Eurasian Patent Office in connection with Eurasian Patent Application No. 201691351.
May 8, 2018 Response to Dec. 12, 2017 Technical Examination Report issued by the Salvadorian Patent Office in connection with Salvadorian Patent Application No. 20160020316.
Apr. 4, 2018 Office Action issued by the Chinese Patent Office in connection with Chinese Patent Application No. 201480076583.4 (English language translation).
Aug. 20, 2018 Response to Apr. 4, 2018 Office Action issued by the Chinese Patent Office in connection with Chinese Patent Application No. 201480076583.4.
Aug. 31, 2018 Office Action issued by the Eurasian Patent Office in connection with Eurasian Patent Application No. 201691351 (including English language translation).
Jul. 17, 2018 Office Action issued by the Israeli Patent Office in connection with Israeli Patent Application No. 246512.
Aug. 21, 2018 Office Action issued by the Japanese Patent Office in connection with Japanese Patent Application No. 2016-543735 (including English language translation).
Apr. 27, 2018 Response to Oct. 2, 2017 Supplementary European Search Report issued by the European Patent Office in connection with European Patent Application No. 14877100.9.
Aug. 21, 2018 Office Action issued by the Japanese Patent Office in connection with Japanese Patent Application No. 2016-543740.
Jun. 8, 2018 First Examination Report issued by the Australian Patent Office in connection with Australian Patent Application No. 2017261457.
Feb. 19, 2018 Office Action issued by the Chilean Patent Office in connection with Chilean Patent Application No. 1676-2016.
Feb. 8, 2018 Office Action issued by the Chinese Patent Office in connection with Chinese Patent Application No. 201480076449.4 (English language translation).
Jun. 25, 2018 Response to Feb. 8, 2018 Office Action issued by the Chinese Patent Office in connection with Chinese Patent Application No. 201480076449.4.
Jan. 10, 2018 Office Action issued by the Colombian Patent Office in connection with Colombian Patent Application No. 2016-0000472.
Mar. 20, 2018 Response to Jan. 10, 2018 Office Action issued by the Colombian Patent Office in connection with Colombian Patent Application No. 2016-0000472.
Jun. 13, 2018 Office Action issued by the Colombian Patent Office in connection with Colombian Patent Application No. 2016-0000472.
Aug. 13, 2018 Response to Jun. 13, 2018 Office Action issued by the Colombian Patent Office in connection with Colombian Patent Application No. 2016-0000472.
May 11, 2018 Response to Mar. 15, 2018 Office Action issued by the Cuban Patent Office in connection with Cuban Patent Application No. 2016-0100.
Office Action issued by the Egyptian Patent Office in connection with Egyptian Patent Application No. PCT1099/2016.
Jun. 8, 2018 First Examination Report issued by the Australian Patent Office in connection with Australian Patent Application No. 2017261458.
Feb. 19, 2018 Office Action issued by the Chilean Patent Office in connection with Chilean Patent Application No. 2016-001678.
Feb. 8, 2018 Office Action issued by the Chinese Patent Office in connection with Chinese Patent Application No. 201480076442.2 (English language translation).
Jun. 25, 2018 Response to Feb. 8, 2018 Office Action issued by the Chinese Patent Office in connection with Chinese Patent Application No. 201480076442.2.
Feb. 12, 2018 Office Action issued by the Colombian Patent Office in connection with Colombian Patent Application No. 2016-0000502.

(56) References Cited

OTHER PUBLICATIONS

May 10, 2018 Response to Feb. 12, 2018 Office Action issued by the Colombian Patent Office in connection with Colombian Patent Application No. 2016-0000502.
Mar. 15, 2018 Office Action issued by the Cuban Patent Office in connection with Cuban Patent Application No. 2016-0103 (including English language translation).
May 17, 2018 Response to Mar. 15, 2018 Office Action issued by the Cuban Patent Office in connection with Cuban Patent Application No. 2016-0103.
Dec. 11, 2017 Response to Jul. 28, 2017 Technical Report issued by the Salvadorian Patent Office in connection with Salvadorian Patent Application No. 20160020322.
Aug. 21, 2018 Office Action issued by the Japanese Patent Office in connection with Japanese Patent Application No. 2016-543745.
Mar. 1, 2018 Response to Aug. 22, 2017 Communication pursuant to Rules 70(2) and 70a(2) issued by the European Patent Office in connection with European Patent Application No. 14876883.1.
Apr. 27, 2018 Response to Sep. 29, 2017 Supplementary European Search Report issued by the European Patent Office in connection with European Patent Application No. 14876118.2.
Jun. 8, 2018 First Examination Report issued by the Australian Patent Office in connection with Australian Patent Application No. 2017261459.
Feb. 20, 2018 Office Action issued by the Chilean Patent Office in connection with Chilean Patent Application No. 2016-1679.
May 17, 2018 Response to Feb. 19, 2018 Office Action issued by the Chilean Patent Office in connection with Chilean Patent Application No. 2016-1679.
Feb. 8, 2018 Office Action issued by the Chinese Patent Office in connection with Chinese Patent Application No. 201480076443.7 (English language translation).
Jun. 25, 2018 Response to Feb. 8, 2018 Office Action issued by the Chinese Patent Office in connection with Chinese Patent Application No. 201480076443.7.
Feb. 13, 2018 Office Action issued by the Colombian Patent Office in connection with Colombian Patent Application No. 2016-0000520.
Mar. 13, 2018 Response to Feb. 13, 2018 Office Action issued by the Colombian Patent Office in connection with Colombian Patent Application No. 2016-0000520.
May 14, 2018 Response to Mar. 15, 2018 Office Action issued by the Cuban Patent Office in connection with Cuban Patent Application No. 2016-0102.
Jul. 26, 2018 Office Action issued by the Dominican Republic Patent Office in connection with Dominican Patent Application No. P2016-0165 (including English language translation).
Aug. 21, 2018 Office Action issued by the Japanese Patent Office in connection with Japanese Patent Application No. 2016-543731.
Apr. 26, 2018 Supplementary European Search Report issued by the European Patent Office in connection with European Patent Application No. 15874200.7.
May 16, 2018 Communication pursuant to Rules 70(2) and 70a(2) EPC issued by the European Patent Office in connection with European Patent Application No. 15874200.7.
Apr. 3, 2018 Office Action issued by the Eurasian Patent Office in connection with Eurasian Patent Application No. 201791444 (including English language translation).
Aug. 3, 2018 Response to Apr. 3, 2018 Office Action issued by the Eurasian Patent Office in connection with Eurasian Patent Application No. 201791444.
Nov. 15, 2017 Office Action issued by the Thai Patent Office in connection with Thai Patent Application No. 1701003629.
Feb. 13, 2018 Response to Nov. 15, 2017 Office Action issued by the Thai Patent Office in connection with Thai Patent Application No. 1701003629.
Oct. 24, 2018 Advisory Action issued by the U.S. Patent and Trademark Office in connection with U.S. Appl. No. 15/813,562.
Nov. 15, 2018 Final Office Action issued by the U.S. Patent and Trademark Office in connection with U.S. Appl. No. 15/813,562.

Nov. 20, 2018 Communication vacating Nov. 15, 2018 Final Office Action issued by the U.S. Patent and Trademark Office in connection with U.S. Appl. No. 15/813,562.
Feb. 21, 2019 Final Office Action issued by the U.S. Patent and Trademark Office in connection with U.S. Appl. No. 15/813,562.
Jan. 23, 2019 Non-Final Office Action issued by the U.S. Patent and Trademark Office in connection with U.S. Appl. No. 16/022,977.
Jan. 23, 2019 Non-Final Office Action issued by the U.S. Patent and Trademark Office in connection with U.S. Appl. No. 16/022,007.
Oct. 30, 2018 Appeal filed in response to Aug. 14, 2018 Decision of Rejection issued by the Costa Rican Patent Office in connection with Costa Rican Patent Application No. 2012-0584.
May 22, 2018 Communication pursuant to Article 94(3) issued by the European Patent Office in connection with European Patent Application No. 14877285.8.
Jan. 16, 2019 Office Action issued by the Belizean Patent Office in connection with Belize Patent Application No. 881.16.
Nov. 16, 2018 Office Action issued by the Chinese Patent Office in connection with Chinese Patent Application No. 201480076563.7 (including English language translation).
Mar. 1, 2018 Response to Nov. 16, 2018 Office Action issued by the Chinese Patent Office in connection with Chinese Patent Application No. 201480076563.7.
Dec. 13, 2018 Office Action issued by the Dominican Republic Patent Office in connection with Dominican Patent Application No. P2016-0163 (including English language translation).
Nov. 18, 2018 Response to Jul. 18, 2018 Office Action issued by the Israeli Patent Office in connection with Israeli Patent Application No. 246511.
Dec. 30, 2018 Office Action issued by the Israeli Patent Office in connection with Israeli Patent Application No. 246511.
Feb. 28, 2019 Response to Aug. 28, 2018 Office Action issued by the Japanese Patent Office in connection with Japanese Patent Application No. 2016-543746.
Feb. 11, 2019 Response to Oct. 9, 2018 Office Action issued by the Mexican Patent Office in connection with Mexican Patent Application No. MX/a/2016/008758.
Aug. 17, 2018 Office Action issued by the Filipino Patent Office in connection with Filipino Patent Application No. 1/2016/501284.
Dec. 6, 2018 Response to Aug. 17, 2018 Office Action issued by the Filipino Patent Office in connection with Filipino Patent Application No. 1/2016/501284.
Oct. 31, 2018 Response to Jul. 31, 2018 Office Action issued by the Taiwanese Patent Office in connection with Taiwanese Patent Application No. 103146555 (including amended claims in English).
Jan. 14, 2019 Office Action issued by the Taiwanese Patent Office in connection with Taiwanese Patent Application No. 103146555.
Nov. 19, 2018 Communication pursuant to Article 94(3) EPC issued by the European Patent Office in connection with European Patent Application No. 14875976.4.
Dec. 10, 2018 Office Action issued by the Chinese Patent Office in connection with Chinese Patent Application No. 201480076583.4 (including English language translation).
Feb. 25, 2019 Response to Dec. 10, 2018 Office Action issued by the Chinese Patent Office in connection with Chinese Patent Application No. 201480076583.4.
Nov. 7, 2018 Response to Jul. 17, 2018 Office Action issued by the Israeli Patent Office in connection with Israeli Patent Application No. 246512.
Dec. 30, 2018 Office Action issued by the Israeli Patent Office in connection with Israeli Patent Application No. 246512.
Jan. 21, 2019 Response to Aug. 21, 2018 Office Action issued by the Japanese Patent Office in connection with Japanese Patent Application No. 2016-543735 (including amended claims in English).
Feb. 19, 2019 Office Action issued by the Japanese Patent Office in connection with Japanese Patent Application No. 2016-543735 (including English language translation).
Sep. 28, 2018 Response to Jul. 6, 2018 Office Action issued by the Thai Patent Office in connection with Thai Patent Application No. 1601003881.
Sep. 19, 2018 Office Action issued by the Taiwanese Patent Office in connection with Taiwan Patent Application No. 103146560.

(56) References Cited

OTHER PUBLICATIONS

Dec. 17, 2018 Response to Sep. 19, 2018 Office Action issued by the Taiwanese Patent Office in connection with Taiwan Patent Application No. 103146560 (including amended claims in English).
Feb. 27, 2019 Response to Jun. 8, 2018 First Examination Report issued by the Australian Patent Office in connection with Australian Patent Application No. 2017261457.
May 16, 2018 Response to Feb. 19, 2018 Office Action issued by the Chilean Patent Office in connection with Chilean Patent Application No. 1676-2016.
Aug. 22, 2018 Office Action issued by the Chilean Patent Office in connection with Chilean Patent Application No. 1676-2016.
Nov. 22, 2018 Response to Aug. 22, 2018 Office Action issued by the Chilean Patent Office in connection with Chilean Patent Application No. 1676-2016.
Nov. 9, 2018 Office Action issued by the Chinese Patent Office in connection with Chinese Patent Application No. 201480076449.4 (including English language translation).
Jan. 24, 2019 Response to Nov. 9, 2018 Office Action issued by the Chinese Patent Office in connection with Chinese Patent Application No. 201480076449.4 (including amended claims in English).
Feb. 12, 2019 Office Action issued by the Cuban Patent Office in connection with Cuban Patent Application No. 2016-0100 (including English language translation).
Dec. 26, 2018 Office Action issued by the Dominican Patent Office in connection with Dominican Patent Application No. P2016-0166 (including English language translation).
Feb. 28, 2019 Response to Oct. 29, 2018 Office Action issued by the Israeli Patent Office in connection with Israeli Patent Application No. 246461.
Nov. 21, 2018 Response to Aug. 21, 2018 Office Action issued by the Japanese Patent Office in connection with Japanese Patent Application No. 2016-543740 (including amended claims in English).
Feb. 19, 2019 Office Action issued by the Japanese Patent Office in connection with Japanese Patent Application No. 2016-543740 (including English language translation).
Feb. 27, 2019 Response to Jun. 8, 2018 First Examination Report issued by the Australian Patent Office in connection with Australian Patent Application No. 2017261458.
May 16, 2018 Response to Feb. 19, 2018 Office Action issued by the Chilean Patent Office in connection with Chilean Patent Application No. 2016-001678.
Aug. 22, 2018 Office Action issued by the Chilean Patent Office in connection with Chilean Patent Application No. 2016-001678.
Nov. 22, 2018 Response to Aug. 22, 2018 Action issued by the Chilean Patent Office in connection with Chilean Patent Application No. 2016-001678.
Nov. 9, 2018 Office Action issued by the Chinese Patent Office in connection with Chinese Patent Application No. 201480076442.2 (including English language translation).
Feb. 25, 2019 Response to Nov. 9, 2018 Office Action issued by the Chinese Patent Office in connection with Chinese Patent Application No. 201480076442.2 (including amended claims in English).
Oct. 30, 2018 Office Action issued by the Colombian Patent Office in connection with Colombian Patent Application No. 2016-0000502.
Feb. 15, 2019 Response to Oct. 30, 2018 Office Action issued by the Colombian Patent Office in connection with Colombian Patent Office in connection with Colombian Patent Application No. 2016-0000502.
Sep. 12, 2018 Office Action issued by the Dominican Patent Office in connection with Dominican Patent Application No. P2016-0164 (including English language translation).
Dec. 6, 2018 Response to Sep. 12, 2018 Office Action issued by the Dominican Patent Office in connection with Dominican Patent Application No. P2016-0164.
Jan. 9, 2019 Office Action issued by the Dominican Patent Office in connection with Dominican Patent Application No. P2016-0164 (including English language translation).
Nov. 21, 2018 Response to Aug. 21, 2018 Office Action issued by the Japanese Patent Office in connection with Japanese Patent Application No. 2016-543745 (including amended claims in English).
Feb. 19, 2019 Office Action issued by the Japanese Patent Office in connection with Japanese Patent Application No. 2016-543745 (including English language translation).
Feb. 27, 2019 Response to Jun. 8, 2018 First Examination Report issued by the Australian Patent Office in connection with Australian Patent Application No. 2017261459.
Aug. 22, 2018 Office Action issued by the Chilean Patent Office in connection with Chilean Patent Application No. 2016-1679.
Nov. 22, 2018 Response to Aug. 22, 2018 Office Action issued by the Chilean Patent Office in connection with Chilean Patent Application No. 2016-1679.
Nov. 9, 2018 Office Action issued by the Chinese Patent Office in connection with Chinese Patent Application No. 201480076443.7 (including English language translation).
Jan. 24, 2019 Response to Nov. 9, 2018 Office Action issued by the Chinese Patent Office in connection with Chinese Patent Application No. 201480076443.7.
Feb. 21, 2019 Office Action issued by the Cuban Patent Office in connection with Cuban Patent Application No. 2016-0102.
Nov. 8, 2018 Response to Jul. 26, 2018 Office Action issued by the Dominican Republic Patent Office in connection with Dominican Patent Application No. P2016-0165.
Dec. 13, 2018 Office Action issued by the Dominican Republic Patent Office in connection with Dominican Patent Application No. P2016-0165.
Oct. 15, 2018 Office Action issued by the Israeli Patent Office in connection with Israeli Patent Application No. 246470.
Nov. 21, 2018 Response to Aug. 21, 2018 Office Action issued by the Japanese Patent Office in connection with Japanese Patent Application No. 2016-543731 (including amended claims in English).
Feb. 19, 2019 Office Action issued by the Japanese Patent Office in connection with Japanese Patent Application No. 2016-543731 (including English language translation).
Nov. 26, 2018 Response to Communication pursuant to Rules 70(2) and 70a(2) EPC issued by the European Patent Office in connection with European Patent Application No. 15874200.7.
Oct. 30, 2018 Office Action issued by the Eurasian Patent Office in connection with Eurasian Patent Application No. 201791444 (including English language translation).
Feb. 28, 2019 Response to Oct. 30, 2018 Office Action issued by the Eurasian Patent Office in connection with Eurasian Patent Application No. 201791444 (including amended claims in English).
Jan. 15, 2019 Office Action issued by the Chilean Patent Office in connection with Chilean Patent Application No. 2017-001686 (including English language translation).
Oct. 19, 2018 Response to Jun. 8, 2018 Final Office Action issued by the U.S. Patent and Trademark Office in connection with U.S. Appl. No. 15/813,562.
Mar. 8, 2019 Response to Office Action issued by the Argentinean Patent Office in connection with Argentinean Patent Application No. 20110101423.
Feb. 15, 2019 Office Action issued by the Filipino Patent Office in connection with Filipino Patent Application No. 1/2012/502138.
Mar. 11, 2019 Office Action issued by the Cuban Patent Office in connection with Cuban Patent Application No. 2016-0103 (including English language translation).
Mar. 17, 2019 Response to Oct. 15, 2018 Office Action issued by the Israeli Patent Office in connection with Israeli Patent Application No. 246470.

SYNERGISTIC FUNGICIDAL MIXTURES AND COMPOSITIONS COMPRISING 5-FLUORO-4-IMINO-3-METHYL-1-TOSYL-3,4-DIHYDROPYRIMIDIN-2(1H)-ONE FOR FUNGAL CONTROL

CROSS REFERENCE TO RELATED APPLICATIONS

This application is a continuation of U.S. Ser. No. 15/377,859, filed Dec. 13, 2016, now U.S. Pat. No. 10,051,862, issued Aug. 21, 2018, which is a continuation of U.S. Ser. No. 14/585,962, filed Dec. 30, 2014, now U.S. Pat. No. 9,538,753, which claims the benefit of U.S. Provisional Patent Application Ser. Nos. 61/922,616, 61/922,630, and 61/922,640, all filed Dec. 31, 2013, which are expressly incorporated by reference herein.

FIELD OF THE INVENTION

This disclosure concerns a synergistic fungicidal composition containing (a) a compound of Formula I and (b) at least one fungicide selected from the group consisting of a strobilurin, for example pyraclostrobin, fluoxastrobin, azoxystrobin, trifloxystrobin, picoxystrobin, and kresoxim-methyl; a succinate dehydrogenase-inhibitor (SDHI), for example fluxapyroxad, benzovindiflupyr, penthiopyrad, isopyrazam, bixafen, boscalid, penflufen, and fluopyram; an ergosterol biosynthesis-inhibitor (SBI), for example prothioconazole, epoxiconazole, cyproconazole, myclobutanil, prochloraz, metconazole, difenoconazole, tebuconazole, tetraconazole, fenbuconazole, propiconazole, fluquinconazole, flusilazole, flutriafol, and fenpropimorph; and a multi-site-inhibitor, for example mancozeb and chlorothalonil, or other commercial fungicides to provide control of any plant fungal pathogen.

BACKGROUND AND SUMMARY

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop, and consequently, increase the value of the crop. In most situations, the increase in value of the crop is worth at least three times the cost of the use of the fungicide.

However, no one fungicide is useful in all situations and repeated usage of a single fungicide frequently leads to the development of resistance to that and related fungicides. Consequently, research is being conducted to produce fungicides and combinations of fungicides that are safer, that have better performance, that require lower dosages, that are easier to use, and that cost less.

Synergism occurs when the activity of two or more compounds exceeds the activities of the compounds when used alone.

It is an object of this disclosure to provide synergistic compositions comprising fungicidal compounds. It is a further object of this disclosure to provide processes that use these synergistic compositions. The synergistic compositions are capable of preventing or curing, or both, diseases caused by fungi of the classes Ascomycetes and Basidiomycetes. In addition, the synergistic compositions have improved efficacy against the Ascomycete and Basidiomycete pathogens, including leaf blotch and brown rust of wheat. In accordance with this disclosure, synergistic compositions are provided along with methods for their use.

According to an exemplary embodiment of the present disclosure, a synergistic fungicidal mixture is provided including a fungicidally effective amount of the compound of Formula I, and at least one fungicidal multi-site inhibitor.

According to another exemplary embodiment of the present disclosure, a synergistic fungicidal mixture is provided including a fungicidally effective amount of the compound of Formula I, and at least additional fungicide in which the at least one additional fungicide is a fungicidal multi-site inhibitor.

According to yet another exemplary embodiment of the present disclosure, a synergistic, fungicidal composition is provided including a fungicidally effective amount of the mixture and an agriculturally acceptable adjuvant or carrier.

In certain embodiments, the multi-site inhibitor and/or the at least one additional fungicide is selected from the group consisting of chlorothalonil and mancozeb.

In certain embodiments, the multi-site inhibitor and/or the at least one additional fungicide is chlorothalonil.

In certain embodiments, the multi-site inhibitor and/or the at least one additional fungicide is mancozeb.

In certain embodiments, the concentration ratio of the Compound of Formula I to chlorothalonil is about 1:219.

In certain embodiments, the concentration ratio of the Compound of Formula I to mancozeb is about 1:272.

In certain embodiments, the mixture provides control of a fungal pathogen and the fungal pathogen is one of Leaf Blotch of Wheat (*Mycosphaerella graminicola*; anamorph; *Septoria tritici*), Wheat Brown Rust (*Puccinia triticina*), Stripe Rust (*Puccinia striiformis* f. sp. *tritici*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

In certain embodiments, the mixture provides control of a fungal pathogen and the fungal pathogen is Leaf Blotch of Wheat (*Mycosphaerella graminicola*; anamorph; *Septoria tritici*).

According to yet another exemplary embodiment of the present disclosure, a synergistic fungicidal mixture is provided including a fungicidally effective amount of the compound of Formula I, and at least one strobilurin fungicide.

According to still yet another exemplary embodiment of the present disclosure, a synergistic fungicidal mixture is provided including a fungicidally effective amount of the compound of Formula I, and at least one additional fungicide in which the at least one additional fungicide is a strobilurin fungicide.

According to still yet another exemplary embodiment of the present disclosure, a synergistic, fungicidal composition is provided including a fungicidally effective amount of the mixture and an agriculturally acceptable adjuvant or carrier.

In certain embodiments, the strobilurin fungicide and/or the at least one additional fungicide is selected from the group consisting of pyraclostrobin, fluoxastrobin, azoxystrobin, trifloxystrobin, picoxystrobin, and kresoxim-methyl.

In certain embodiments, the strobilurin fungicide and/or the at least one additional fungicide is pyraclostrobin.

In certain embodiments, the strobilurin fungicide and/or the at least one additional fungicide is azoxystrobin.

In certain embodiments, the concentration ratio of the Compound of Formula I to picoxystrobin is between about 1:30 and about 1:2.6.

In certain embodiments, the concentration ratio of the Compound of Formula I to trifloxystrobin is between about 1:9.7 and about 4:1.

In certain embodiments, the concentration ratio of the Compound of Formula I to azoxystrobin is between about 1:4.6 and about 2:1.

In certain embodiments, the concentration ratio of the Compound of Formula I to fluoxastrobin is between about 1:1.6 and about 7:1.

In certain embodiments, the concentration ratio of the Compound of Formula I to kresoxim-methyl is between about 1:250 and about 1:21.2.

In certain embodiments, the mixture provides control of a fungal pathogen and the fungal pathogen is one of Leaf Blotch of Wheat (*Mycosphaerella graminicola*; anamorph; *Septoria tritici*), Wheat Brown Rust (*Puccinia triticina*), Stripe Rust (*Puccinia striiformis* f. sp. *tritici*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

In certain embodiments, the mixture provides control of a fungal pathogen and the fungal pathogen is Leaf Blotch of Wheat (*Mycosphaerella graminicola*; anamorph; *Septoria tritici*).

DETAILED DESCRIPTION

The present disclosure concerns a synergistic fungicidal mixture comprising a fungicidally effective amount of (a) a compound of Formula I and (b) at least one fungicide selected from the group consisting of a strobilurin, for example pyraclostrobin, fluoxastrobin, azoxystrobin, trifloxystrobin, picoxystrobin, and kresoxim-methyl, a succinate dehydrogenase-inhibitor, for example fluxapyroxad, benzovindiflupyr, penthiopyrad, isopyrazam, bixafen, boscalid, penflufen, and fluopyram, an ergosterol biosynthesis-inhibitor, for example prothioconazole, epoxiconazole, cyproconazole, myclobutanil, prochloraz, metconazole, difenoconazole, tebuconazole, tetraconazole, fenbuconazole, propiconazole, fluquinconazole, flusilazole, flutriafol, fenpropimorph, and prochloaz, and a multi-site-inhibitor, for example mancozeb and chlorothalonil, or other commercial fungicides to provide control of any plant fungal pathogen.

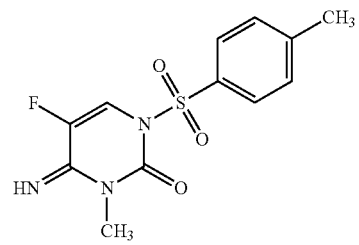

Formula I

As used herein, the compound of Formula I is 5-fluoro-4-imino-3-methyl-1-tosyl-3,4-dihydropyrimidin-2(1H)-one. The compound of Formula I provides control of a variety of pathogens in economically important crops including, but not limited to, the causal agent of leaf blotch in wheat, *Septoria tritici* (SEPTTR).

As used herein, epoxiconazole is the common name for (2RS,3SR)-1-[3-(2-chlorophenyl)-2,3-epoxy-2-(4-fluorophenyl)propyl]-1H-1,2,4-triazole and possesses the following structure:

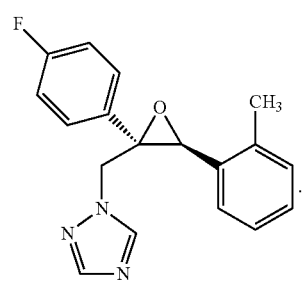 [SMILES: Cc1ccccc1[C@@H]1O[C@@]1(Cn1cncn1)c1ccc(F)cc1]

Its fungicidal activity is described in *The Pesticide Manual*, Fifteenth Edition, 2009. Epoxiconazole provides broad spectrum control, with preventive and curative action, of diseases caused by Ascomycetes, Basidiomycetes and Deuteromycetes in bananas, cereals, coffee, rice and sugar beet.

As used herein, cyproconazole is the common name for (2RS,3RS;2RS,3SR)-2-(4-chlorophenyl)-3-cyclopropyl-1-(1H-1,2,4-triazol-1-yl)butan-2-ol and possesses the following structure:

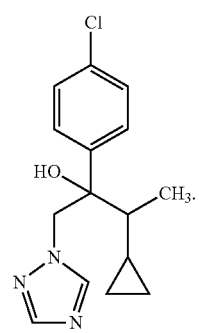

Its fungicidal activity is described in *The Pesticide Manual*, Fifteenth Edition, 2009. Cyproconazole provides control of *Septoria*, rust, powdery mildew, *Rhynchosporium*, *Cercospora* and *Ramularia* in cereals and sugar beet; and rust, *Mycena*, *Sclerotinia* and *Rhizoctonia* in coffee and turf.

As used herein, metconazole is the common name for (1RS,5RS;1RS,5SR)-5-(4-chlorobenzyl)-2,2-dimethyl-1-(1H-1,2,4-triazol-1-ylmethyl)cyclopentanol and possesses the following structure:

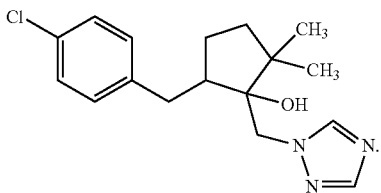 [SMILES: CC1(C)CCC(Cc2ccc(Cl)cc2)C1(O)Cn1cncn1]

Its fungicidal activity is described in *The Pesticide Manual*, Fifteenth Edition, 2009. Metconazole provides control of a wide range of foliar diseases on cereals and other crops, and is particularly effective against *Fusarium, Septoria* and rust diseases on cereals.

As used herein, myclobutanil is the common name for α-butyl-α-(4-chlorophenyl)-1H-1,2,4-triazole-1-propanenitrile and possesses the following structure:

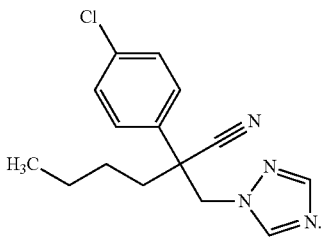

Its fungicidal activity is described in *The Pesticide Manual*, Fifteenth Edition, 2009. Myclobutanil provides control of Ascomycetes, Fungi Imperfecti and Basidiomycetes on a wide variety of crops.

As used herein, propiconazole is the common name for (±)-1-[2-(2,4-dichlorophenyl)-4-propyl-1,3-dioxolan-2-ylmethyl]-1H-1,2,4-triazole and possesses the following structure:

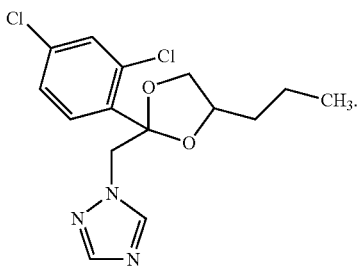 [SMILES: CCCC1COC(Cn2cncn2)(c2ccc(Cl)cc2Cl)O1]

Its fungicidal activity is described in *The Pesticide Manual*, Fifteenth Edition, 2009. Propiconazole provides control of a broad range of diseases on a variety of crops. For example, on cereals it controls diseases caused by *Cochliobolus sativus, Erysiphe graminis, Leptosphaeria nodorum, Puccinia* spp., *Pyrenophora teres, Pyrenophora tritici-repentis, Rhynchosporium secalis* and *Septoria* spp, and in bananas it controls diseases caused by *Mycosphaerella musicola* and *Mycosphaerella fijiensis* var. *difformis*. Other uses are in turf, against *Sclerotinia homoeocarpa, Rhizoctonia solani, Puccinia* spp. and *Erysiphe graminis*; in rice, against *Rhizoctonia solani, Helminthosporium oryzae* and dirty panicle complex; in coffee, against *Hemileia vastatrix*; in peanuts, against *Cercospora* spp.; in stone fruit, against *Monilinia* spp., *Podosphaera* spp., *Sphaerotheca* spp. and *Tranzschelia* spp.; and in maize, against *Helminthosporium* spp.

As used herein, prothioconazole is the common name 2-[(2RS)-2-(1-chlorocyclopropyl)-3-(2-chlorophenyl)-2-hydroxypropyl]-2H-1,2,4-triazole-3(4H)-thione and possesses the following structure:

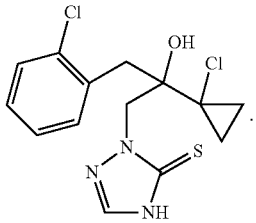 [SMILES: OC(Cc1ccccc1Cl)(Cn1nc[nH]c1=S)C1(Cl)CC1]

Its fungicidal activity is described in *The Pesticide Manual*, Fifteenth Edition, 2009. Prothioconazole provides control of diseases such as eyespot (*Pseudocercosporella herpotrichoides*), Fusarium ear blight (*Fusarium* spp., *Microdochium nivale*), leaf blotch diseases (*Septoria tritici, Leptosphaeria nodorum, Pyrenophora* spp., *Rhynchosporium secalis*, etc.), rust (*Puccinia* spp.) and powdery mildew (*Blumeria graminis*), by foliar application, in wheat, barley and other crops.

As used herein, picoxystrobin is the common name for methyl (E)-3-methoxy-2-[2-(6-trifluoromethyl-2-pyridyloxymethyl)phenyl]acylate and possesses the following structure:

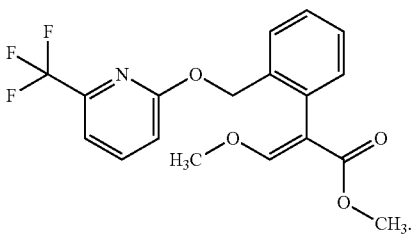 [SMILES: CO/C=C(/C(=O)OC)c1ccccc1COc1cccc(C(F)(F)F)n1]

Its fungicidal activity is described in *The e-Pesticide Manual*, Version 5.2, 2011. Exemplary uses of picoxystrobin include, but are not limited to, broad-spectrum disease control in cereals, including *Mycosphaerella graminicola, Phaeosphaeria nodorum, Puccinia recondita* (brown rust), *Helminthosporium tritici-repentis* (tan spot) and *Blumeria graminis* f.sp. *tritici* (strobilurin-sensitive powdery mildew) in wheat; *Helminthosporium teres* (net blotch), *Rhynchosporium secalis, Puccinia hordei* (brown rust) and *Erysiphe graminis* f.sp. *hordei* (strobilurin-sensitive powdery mildew) in barley; *Puccinia coronata* and *Helminthosporium avenae* in oats; and *Puccinia recondita* and *Rhynchosporium secalis* in rye.

As used herein, trifloxystrobin is the common name for methyl (αE)-α-(methoxyimino)-2-[[[[(1E)-1-[3-(trifluoromethyl)phenyl]ethylidene]amino]oxy]methyl]-benzeneacetate and possesses the following structure:

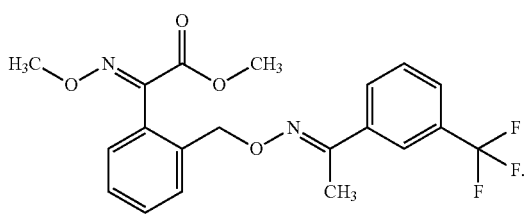 [SMILES: CO/N=C(/C(=O)OC)c1ccccc1CO/N=C(\C)c1cccc(C(F)(F)F)c1]

Its fungicidal activity is described in *The Pesticide Manual*, Fifteenth Edition, 2009. Trifloxystrobin provides broad-spectrum control of a variety of fungal pathogens on a wide variety of fruits, vegetables, and crops.

As used herein, azoxystrobin is the common name for methyl (E)-2-{2-[6-(2-cyanophenoxy)pyrimidin-4-yloxy]phenyl}-3-methoxyacrylate and possesses the following structure:

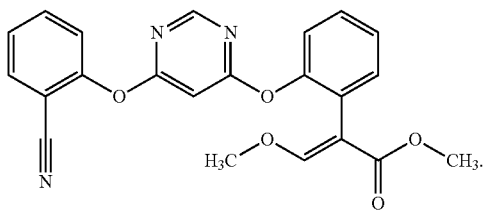 [SMILES: CO/C=C(/C(=O)OC)c1ccccc1Oc1cc(Oc2ccccc2C#N)ncn1]

Its fungicidal activity is exemplified in *The e-Pesticide Manual*, Version 5.2, 2011. Exemplary uses of azoxystrobin include, but are not limited to, control of the following pathogens: *Erysiphe graminis, Puccinia* spp., *Leptosphaeria nodorum, Septoria tritici* and *Pyrenophora teres* on temperate cereals; *Pyricularia oryzae* and *Rhizoctonia solani* on rice; *Plasmopara viticola* and *Uncinula necator* on vines; *Sphaerotheca fuliginea* and *Pseudoperonospora cubensis* on cucurbitaceae; *Phytophthora infestans* and *Alternaria solani* on potato and tomato; *Mycosphaerella arachidis, Rhizocionia solani* and *Sclerotium rolfsii* on peanut; *Monilinia* spp. and *Cladosporium carpophilum* on peach; *Pythium* spp. and *Rhizoctonia solani* on turf; *Mycosphaerella* spp. on banana; *Cladosporium caryigenum* on pecan; *Elsinoë fawcettii, Colletotrichum* spp. and *Guignardia citricarpa* on citrus; *Colletotrichum* spp. and *Hemileia vastatrix* on coffee.

As used herein, fluoxastrobin is the common name for (E)-{2-[6-(2-chlorophenoxy)-5-fluoropyrimidin-4-yloxy]phenyl}(5,6-dihydro-1,4,2-dioxazin-3-yl)methanone O-methyloxime and possesses the following structure:

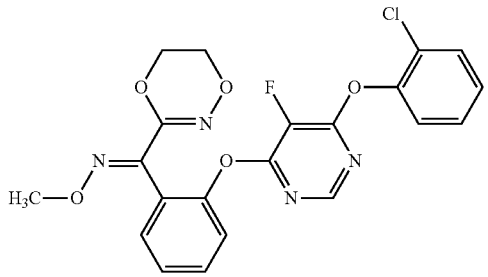

Its fungicidal activity is exemplified in *The e-Pesticide Manual*, Version 5.2, 2011. Exemplary uses of fluoxastrobin include, but are not limited to, use as a foliar spray in cereals for control of *Septoria* leaf spot diseases (*Septoria tritici* and *Leptosphaeria nodorum*), rusts of wheat and barley (*Puccinia recondita, P. striiformis, P. hordei*), *Helminthosporium* diseases like *Pyrenophora teres* (net blotch of barley) and *Pyrenophora tritici-repentis* (tan spot).

As used herein, boscalid is the common name for 2-chloro-N-(4'-chloro[1,1'-biphenyl]-2-yl)-3-pyridinecarboxamide and possesses the following structure:

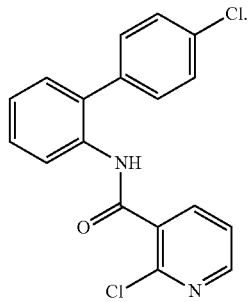 [SMILES: O=C(Nc1ccccc1-c1ccc(Cl)cc1)c1cccnc1Cl]

Its fungicidal activity is described in *The Pesticide Manual*, Fifteenth Edition, 2009. Boscalid provides control of powdery mildew, *Alternaria* spp., *Botrytis* spp., *Sclerotinia* spp., *Mycosphaerella* spp. and *Monilia* spp. on grapes, turf, and a range of fruit, vegetables and ornamentals.

As used herein, isopyrazam is the common name for a mixture of the 2 syn and 2 anti isomers of 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide, respectively, and possesses the following structures:

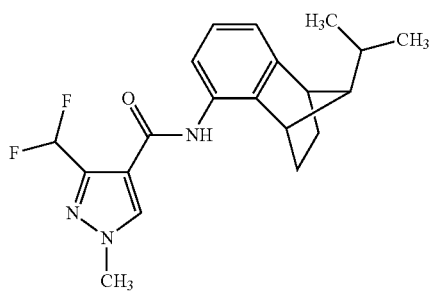

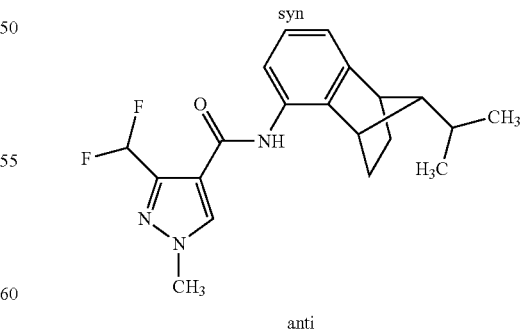

Its fungicidal activity is described in *The Pesticide Manual*, Fifteenth Edition, 2009. Isopyrazam provides control of *Septoria tritici* and rusts in wheat, and *Ramularia* in barley.

As used herein, fluxapyroxad is the common name for 3-(difluoromethyl)-1-methyl-N-(3',4',5'-trifluorobiphenyl-2-yl)pyrazole-4-carboxamide and possesses the following structure:

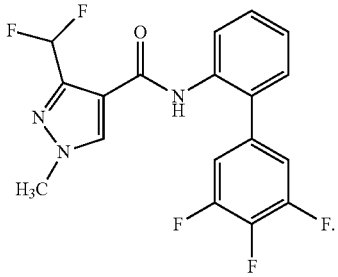 [SMILES: Cn1cc(C(=O)Nc2ccccc2-c2cc(F)c(F)c(F)c2)c(C(F)F)n1]

Its fungicidal activity is exemplified in Agrow Intelligence (https://www.agra-net.net/agra/agrow/databases/agrow-intelligence/). Exemplary uses of fluxapyroxad include, but are not limited to, the control of plant pathogens, such as *Helminthosporium teres* (net blotch), *Rhynchosporium secalis* (leaf scald), *Puccinia hordei* (brown rust), and *Erysiphe graminis* f.sp. *hordei* (powdery mildew) in a range of crops, such as barley, maize, and soybeans.

As used herein, penthiopyrad is the common name for N-[2-(1,3-dimethylbutyl)-3-thienyl]-1-methyl-3-(trifluoromethyl)-1H-pyrazole-4-carboxamide and possesses the following structure:

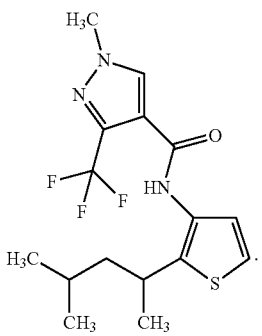 [SMILES: CC(C)CC(C)c1sccc1NC(=O)c1cn(C)nc1C(F)(F)F]

Its fungicidal activity is described in *The Pesticide Manual*, Fifteenth Edition, 2009. Penthiopyrad provides control of rust and *Rhizoctonia* diseases, as well as grey mold, powdery mildew and apple scab.

As used herein, benzovindiflupyr is the common name for N-[(1RS,4SR)-9-(dichloromethylene)-1,2,3,4-tetrahydro-1,4-methanonaphthalen-5-yl]-3-(difluoromethyl)-1-methyl-pyrazole-4-carboxamide and possesses the following structure:

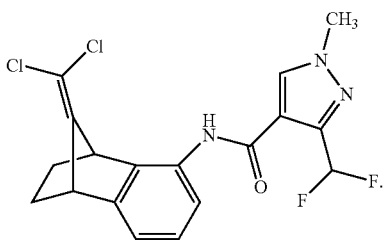 [SMILES: Cn1cc(C(=O)Nc2cccc3c2C2CCC3C2=C(Cl)Cl)c(C(F)F)n1]

Its fungicidal activity is exemplified in Agrow Intelligence (https://www.agra-net.net/agra/agrow/databases/agrow-intelligence). Exemplary uses of benzovindiflupyr include, but are not limited to, controlling a variety of pathogens such as *Botrytis* spp., *Erysiphe* spp., *Rhizoctonia* spp., *Septoria* spp., *Phytophthora* spp., *Pythium* spp., *Phakopsora pachyrhizi*, and *Puccinia recondita*, in a range of crops including vines, cereals, soybeans, cotton, and fruit and vegetable crops.

As used herein, fluquinconazole is the common name for 3-(2,4-dichlorophenyl)-6-fluoro-2-(1H-1,2,4-triazol-1-yl)quinazolin-4(3H)-one and possesses the following structure:

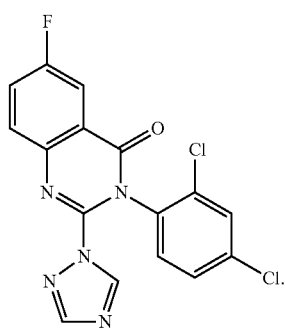 [SMILES: O=c1c2cc(F)ccc2nc(-n2cncn2)n1-c1ccc(Cl)cc1Cl]

Its fungicidal activity is described in *The Pesticide Manual*, Fifteenth Edition, 2009. Fluquinconazole provides control of a wide range of Ascomycetes. Deuteromycetes and Basidiomycetes. For example, foliar application provides control of *Leptosphaeria nodorum, Septoria tritici, Puccinia* spp., *Ustilago nuda, Tilletia caries, Tilletia controversa, Urocystis occulta, Pyrenophora teres*, and *Pyrenophora graminea* in cereals; *Cercospora* spp., *Microsphaera diffusa*, and *Phakopsora pachyrhizi* in soybeans; *Venturia* spp., and *Podosphaera leucotricha* in pome fruit; and *Uncinula necator* in vines.

As used herein, difenoconazole is the common name for 1-[[2-[2-chloro-4-(4-chlorophenoxy)phenyl]-4-methyl-1,3-dioxolan-2-yl]methyl]-1H-1,2,4-triazole and possesses the following structure:

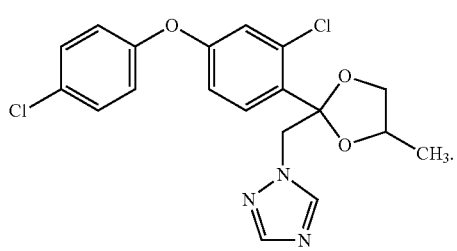 [SMILES: CC1COC(Cn2cncn2)(c2ccc(Oc3ccc(Cl)cc3)cc2Cl)O1]

Its fungicidal activity is described in *The Pesticide Manual*, Fifteenth Edition, 2009. Difenoconazole provides broad-spectrum fungicidal control, with preventative and curative action, of diseases caused by Ascomycetes, Basidiomycetes and Deuteromycetes.

As used herein, pyraclostrobin is the common name for methyl N-[2-[[[1-(4-chlorophenyl)-1H-pyrazol-3-yl]oxy]methyl]phenyl]-N-methoxycarbamate and possesses the following structure:

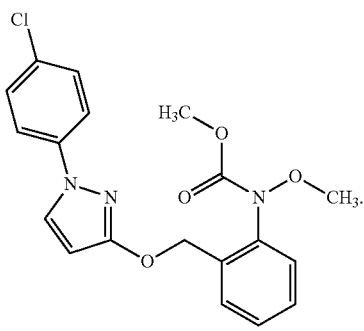 [SMILES: COC(=O)N(OC)c1ccccc1COc1ccn(-c2ccc(Cl)cc2)n1]

Its fungicidal activity is exemplified in *The e-Pesticide Manual*, Version 5.2, 2011. Exemplary uses of pyraclostrobin include, but are not limited to, the control of major plant pathogens, such as *Septoria tritici*, *Puccinia* spp., *Drechslera tritici-repentis* and *Pyrenophora teres* in cereals.

As used herein, fluopyram is the common name for N-[2-[3-chloro-5-(trifluoromethyl)-2-pyridinyl]ethyl]-2-(trifluoromethyl)benzamide and possesses the following structure:

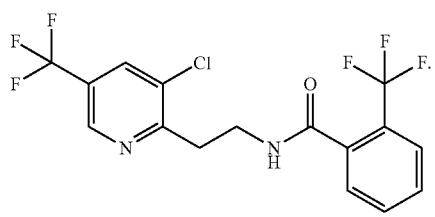 [SMILES: O=C(NCCc1ncc(C(F)(F)F)cc1Cl)c1ccccc1C(F)(F)F]

Its fungicidal activity is described in *The Pesticide Manual*, Fifteenth Edition, 2009. Fluopyram provides control of grey mold, powdery mildew and *sclerotinia* and *monilinia* diseases in a variety of fruits, vegetables and field crops.

As used herein, flutriafol is the common name for (RS)-2,4'-difluoro-α-(1H-1,2,4-triazol-1-ylmethyl)benzhydryl alcohol and possesses the following structure:

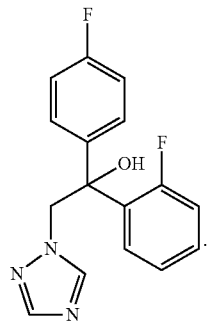 [SMILES: OC(Cn1cncn1)(c1ccc(F)cc1)c1ccccc1F]

Its fungicidal activity is described in *The Pesticide Manual*, Fifteenth Edition, 2009. Flutriafol provides control of a broad spectrum of leaf and ear diseases, including but not limited to, *Erysiphe graminis, Rhynchosporium secalis, Septoria* spp., *Puccinia* spp., *Helminthosporium teres* and *Helminthosporium tritici-repentis* in cereals.

As used herein, kresoxim-methyl is the common name for methyl (E)-methoxyimino[2-(o-tolyloxymethyl)phenyl]acetate and possesses the following structure:

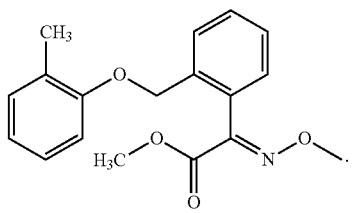 [SMILES: CO/N=C(/C(=O)OC)c1ccccc1COc1ccccc1C]

Its fungicidal activity is exemplified in *The e-Pesticide Manual*, Version 5.2, 2011. Exemplary uses of kresoxim-methyl include, but are not limited to, the control of scab in apples and pears (*Venturia* spp.); powdery mildew on apples (*Podosphaera leucotricha*), vines (*Uncinula necator*), cucurbits (*Sphaerotheca fuliginea*) and sugar beet (*Erysiphe betae*); mildew (*Erysiphe graminis*), scald (*Rhynchosporium secalis*), net blotch (*Pyrenophora teres*) and glume blotch (*Septoria nodorum*) on cereals; and mildew (*Leveillula taurica, Erysiphe* spp., *Alternaria* spp.) on vegetables.

As used herein, chlorothalonil is the common name tetrachloroisophthalonitrile and possesses the following structure:

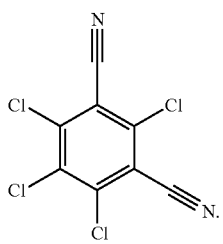 [SMILES: N#Cc1c(Cl)c(Cl)c(Cl)c(C#N)c1Cl]

Its fungicidal activity is described in *The Pesticide Manual*, Fifteenth Edition, 2009. Chlorothalonil provides control of many fungal diseases in a wide range of crops, including pome fruit, stone fruit, almonds, citrus fruit, bush and cane fruit, cranberries, strawberries, pawpaws, bananas, mangoes, coconut palms, oil palms, rubber, pepper, vines, hops, vegetables, cucurbits, tobacco, coffee, tea, rice, soybeans, peanuts, potatoes, sugar beet, cotton, maize, ornamentals, mushrooms, and turf.

As used herein, mancozeb is the common name for [[2-[(dithiocarboxy)amino]ethyl]carbamodithioato(2-)-κS, κS']manganese mixture with [[2-[(dithiocarboxy)amino]ethyl]carbamodithioato(2-)-κS,κS']zinc and possesses the following structure:

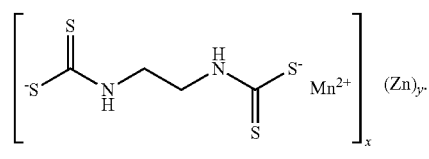

x:y = 1:0.091

Its fungicidal activity is described in *The Pesticide Manual*, Fifteenth Edition, 2009. Mancozeb provides control of a wide range of fungal pathogens on a variety of fruits, vegetables and field crops.

In the compositions described herein, the concentration ratio of the compound of Formula I at which the fungicidal effect is synergistic with the other fungicides against SEP- TTR in protectant and curative applications lies within the range of about 1:250 and about 787:1. In one embodiment, the concentration ratio of the compound of Formula I at which the fungicidal effect is synergistic with the other fungicides in protectant applications lies within the range of about 1:272 and about 787:1. In another embodiment, the concentration ratio of the compound of Formula I at which the fungicidal effect is synergistic with the other fungicides in curative applications lies within the range of about 1:250 and about 120:1.

In the compositions described herein, the concentration ratio of the compound of Formula I at which the fungicidal effect is synergistic with the SBIs against SEPTTR in protectant and curative applications lies within the range of about 1:27 and about 787:1. In one embodiment, the concentration ratio of the compound of Formula I at which the fungicidal effect is synergistic with the SBIs against SEPTTR in protectant applications lies within the range of about 1:4 and about 787:1. In another embodiment, the concentration ratio of the compound of Formula I at which the fungicidal effect is synergistic with the SBIs against SEPTTR in curative applications lies within the range of about 1:27 and about 120:1. In some embodiments, the concentration ratio of the compound of Formula I at which the fungicidal effect is synergistic with epoxiconazole against SEPTTR in protectant and curative applications lies within the range of about 3.6:1 and about 20:1. In one embodiment, the concentration ratio of the compound of Formula I at which the fungicidal effect is synergistic with epoxiconazole against SEPTTR in protectant applications is about 20:1, and in another embodiment, the concentration ratio of the compound of Formula I at which the fungicidal effect is synergistic with epoxiconazole against SEPTTR in curative applications is about 3.6:1. In some embodiments, the concentration ratio of the compound of Formula I at which the fungicidal effect is synergistic with cyproconazole against SEPTTR in protectant and curative applications lies within the range of about 1:3 and about 4.5:1. In one embodiment, the concentration ratio of the compound of Formula I at which the fungicidal effect is synergistic with cyproconazole against SEPTTR in protectant applications is about 4.5:1, and in another embodiment, the concentration ratio of the compound of Formula I at which the fungicidal effect is synergistic with cyproconazole against SEPTTR in curative applications is about 1:3. In some embodiments, the concentration ratio of the compound of Formula I at which the fungicidal effect is synergistic with metconazole against SEPTTR in protectant and curative applications lies within the range of about 2.2:1 and about 30:1. In one embodiment, the concentration ratio of the compound of Formula I at which the fungicidal effect is synergistic with metconazole against SEPTTR in protectant applications is about 30:1, and in another embodiment, the concentration ratio of the compound of Formula I at which the fungicidal effect is synergistic with metconazole against SEPTTR in curative applications is about 2.2:1. In some embodiments, the concentration ratio of the compound of Formula I at which the fungicidal effect is synergistic with myclobutanil against SEPTTR in protectant and curative applications lies within the range of about 1:27 and about 1:4. In one embodiment, the concentration ratio of the compound of Formula I at which the fungicidal effect is synergistic with the myclobutanil against SEPTTR in protectant applications is about 1:4, and in another embodiment, the concentration ratio of the compound of Formula I at which the fungicidal effect is synergistic with myclobutanil against SEPTTR in curative applications is about 1:27. In some embodiments, the concentration ratio of the compound of Formula I at which the fungicidal effect is synergistic with propiconazole against SEPTTR in protectant and curative applications lies within the range of about 1:2.1 and about 30:1. In one embodiment, the concentration ratio of the compound of Formula I at which the fungicidal effect is synergistic with propiconazole against SEPTTR in protectant applications is about 30:1, and in another embodiment, the concentration ratio of the compound of Formula I at which the fungicidal effect is synergistic with propiconazole against SEPTTR in curative applications is about 1:2.1. In some embodiments, the concentration ratio of the compound of Formula I at which the fungicidal effect is synergistic with prothioconazole against SEPTTR in protectant and curative applications lies within the range of about 1:21.6 and about 2:1. In one embodiment, the concentration ratio of the compound of Formula I at which the fungicidal effect is synergistic with prothioconazole against SEPTTR in protectant applications is about 2:1, and in another embodiment, the concentration ratio of the compound of Formula I at which the fungicidal effect is synergistic with prothioconazole against SEPTTR in curative applications is about 1:21.6. In some embodiments, the concentration ratio of the compound of Formula I at which the fungicidal effect is synergistic with fluquinconazole against SEPTTR in protectant and curative applications lies within the range of about 1:1.3 and about 170:1. In one embodiment, the concentration ratio of the compound of Formula I at which the fungicidal effect is synergistic with the fluquinconazole against SEPTTR in protectant applications is about 170:1, and in another embodiment, the concentration ratio of the compound of Formula I at which the fungicidal effect is synergistic with fluquinconazole against SEPTTR in curative applications is about 1:1.3. In some embodiments, the concentration ratio of the compound of Formula I at which the fungicidal effect is synergistic with difenoconazole against SEPTTR in protectant and curative applications lies within the range of about 120:1 and about 787:1. In one embodiment, the concentration ratio of the compound of Formula I at which the fungicidal effect is synergistic with difenoconazole against SEPTTR in protectant applications is about 787:1, and in another embodiment, the concentration ratio of the compound of Formula I at which the fungicidal effect is synergistic with difenoconazole against SEPTTR in curative applications is about 120:1. In some embodiments, the concentration ratio of the compound of Formula I at which the fungicidal effect is synergistic with flutriafol against SEPTTR in protectant and curative applications lies within the range of about 1:20.6 and about 5.1:1. In one embodiment, the concentration ratio of the compound of Formula I at which the fungicidal effect is synergistic with flutriafol against SEPTTR in protectant applications is about 5.1:1, and in another embodiment, the concentration ratio of the compound of Formula I at which the fungicidal effect is synergistic with flutriafol against SEPTTR in curative applications is about 1:20.6.

In the compositions described herein, the concentration ratio of the compound of Formula I at which the fungicidal effect is synergistic with the strobilurins against SEPTTR in protectant and curative applications lies within the range of about 1:250 and about 42:1. In one embodiment, the concentration ratio of the compound of Formula I at which the fungicidal effect is synergistic with the strobilurins against SEPTTR in protectant applications lies within the range of about 1:21.2 and about 42:1. In another embodiment, the concentration ratio of the compound of Formula I at which the fungicidal effect is synergistic with the strobilurins against SEPTTR in curative applications lies within the range of about 1:250 and about 20:1. In some embodiments, the concentration ratio of the compound of Formula I at which the fungicidal effect is synergistic with picoxystrobin against SEPTTR in protectant and curative applications lies within the range of about 1:30 and about 1:2.6. In one embodiment, the concentration ratio of the compound of Formula I at which the fungicidal effect is synergistic with picoxystrobin against SEPTTR in protectant applications is about 1:2.6, and in another embodiment, the concentration ratio of the compound of Formula I at which the fungicidal effect is synergistic with picoxystrobin against SEPTTR in curative applications lies is about 1:30. In some embodiments, the concentration ratio of the compound of Formula I at which the fungicidal effect is synergistic with trifloxystrobin against SEPTTR in protectant and curative applications lies within the range of about 1:9.7 and about 4:1. In one embodiment, the concentration ratio of the compound of Formula I at which the fungicidal effect is synergistic with trifloxystrobin against SEPTTR in protectant applications is about 4:1, and in another embodiment, the concentration ratio of the compound of Formula I at which the fungicidal effect is synergistic with trifloxystrobin against SEPTTR in curative applications is about 1:9.7. In some embodiments, the concentration ratio of the compound of Formula I at which the fungicidal effect is synergistic with azoxystrobin against SEPTTR in protectant and curative applications lies within the range of about 1:4.6 and about 2:1. In one embodiment, the concentration ratio of the compound of Formula I at which the fungicidal effect is synergistic with azoxystrobin against SEPTTR in protectant applications is about 2:1, and in another embodiment, the concentration ratio of the compound of Formula I at which the fungicidal effect is synergistic with azoxystrobin against SEPTTR in curative applications is about 1:4.6. In some embodiments, the concentration ratio of the compound of Formula I at which the fungicidal effect is synergistic with fluoxastrobin against SEPTTR in protectant and curative applications lies within the range of about 1:1.6 and about 7:1. In one embodiment, the concentration ratio of the compound of Formula I at which the fungicidal effect is synergistic with fluoxastrobin against SEPTTR in protectant applications is about 7:1, and in another embodiment, the concentration ratio of the compound of Formula I at which the fungicidal effect is synergistic with fluoxastrobin against SEPTTR in curative applications is about 1:1.6. In some embodiments, the concentration ratio of the compound of Formula I at which the fungicidal effect is synergistic with pyraclostrobin against SEPTTR in protectant and curative applications lies within the range of about 20:1 and about 42:1. In one embodiment, the concentration ratio of the compound of Formula I at which the fungicidal effect is synergistic with pyraclostrobin against SEPTTR in protectant applications is about 42:1, and in another embodiment, the concentration ratio of the compound of Formula I at which the fungicidal effect is synergistic with pyraclostrobin against SEPTTR in curative applications is about 20:1. In some embodiments, the concentration ratio of the compound of Formula I at which the fungicidal effect is synergistic with kresoxim-methyl against SEPTTR in protectant and curative applications lies within the range of about 1:250 and about 1:21.2. In one embodiment, the concentration ratio of the compound of Formula I at which the fungicidal effect is synergistic with kresoxim-methyl against SEPTTR in protectant applications is about 1:21.2, and in another embodiment, the concentration ratio of the compound of Formula I at which the fungicidal effect is synergistic with kresoxim-methyl against SEPTTR in curative applications is about 1:250.

In the compositions described herein, the concentration ratio of the compound of Formula I at which the fungicidal effect is synergistic with the SDHIs against SEPTTR in protectant and curative applications lies within the range of about 1:28 and about 8:1. In one embodiment, the concentration ratio of the compound of Formula I at which the fungicidal effect is synergistic with the SDHIs against SEPTTR in protectant applications lies within the range of about 1:3.6 and about 8:1. In another embodiment, the concentration ratio of the compound of Formula I at which the fungicidal effect is synergistic with the SDHIs against SEPTTR in curative applications lies within the range of about 1:28 and about 6.3:1. In some embodiments, the concentration ratio of the compound of Formula I at which the fungicidal effect is synergistic with boscalid against SEPTTR in protectant and curative applications lies within the range of about 1:13.2 and about 1:1.3. In one embodiment, the concentration ratio of the compound of Formula I at which the fungicidal effect is synergistic with boscalid against SEPTTR in protectant applications is about 1:1.3, and in another embodiment, the concentration ratio of the compound of Formula I at which the fungicidal effect is synergistic with boscalid against SEPTTR in curative applications is about 1:13.2. In some embodiments, the concentration ratio of the compound of Formula I at which the fungicidal effect is synergistic with isopyrazam against SEPTTR in protectant and curative applications lies within the range of about 1:1.3 and about 1:1. In one embodiment, the concentration ratio of the compound of Formula I at which the fungicidal effect is synergistic with isopyrazam against SEPTTR in protectant applications is about 1:1.3, and in another embodiment, the concentration ratio of the compound of Formula I at which the fungicidal effect is synergistic with isopyrazam against SEPTTR in curative applications is about 1:1. In some embodiments, the concentration ratio of the compound of Formula I at which the fungicidal effect is synergistic with fluxapyroxad against SEPTTR in protectant and curative applications lies within the range of about 4.4:1 and about 6.3:1. In one embodiment, the concentration ratio of the compound of Formula I at which the fungicidal effect is synergistic with fluxapyroxad against SEPTTR in protectant applications is about 4.4:1, and in another embodiment, the concentration ratio of the compound of Formula I at which the fungicidal effect is synergistic with fluxapyroxad against SEPTTR in curative applications is about 6.3:1. In some embodiments, the concentration ratio of the compound of Formula I at which the fungicidal effect is synergistic with penthiopyrad against SEPTTR in protectant and curative applications lies within the range of about 1:4.3 and about 1:1.9. In one embodiment, the concentration ratio of the compound of Formula I at which the fungicidal effect is synergistic with penthiopyrad against SEPTTR in protectant applications is about 1:1.9, and in another embodiment, the concentration ratio of the compound of Formula I at which the fungicidal effect is synergistic with penthiopyrad against SEPTTR in curative applications is about 1:4.3. In some embodiments, the concentration ratio of the compound of Formula I at which the fungicidal effect is synergistic with benzovindiflupyr against SEPTTR in protectant and curative applications lies within the range of about 1:3 and about 7.9:1. In one embodiment, the concentration ratio of the compound of Formula I at which the fungicidal effect is synergistic with benzovindiflupyr against SEPTTR in protectant applications is about 7.9:1, and in another embodiment, the concentration ratio of the compound of Formula I at which the fungicidal effect is synergistic with benzovindiflupyr against SEPTTR in curative applications is about 1:3. In some embodiments, the concentration ratio of the compound of Formula I at which the fungicidal effect is synergistic with fluopyram against SEPTTR in protectant and curative applications lies within the range of about 1:27.6 and about 1:3.6. In one embodiment, the concentration ratio of the compound of Formula I at which the fungicidal effect is synergistic with fluopyram against SEPTTR in protectant applications is about 1:3.6, and in another embodiment, the concentration ratio of the compound of Formula I at which the fungicidal effect is synergistic with fluopyram against SEPTTR in curative applications is about 1:27.6.

In the compositions described herein, the concentration ratio of the compound of Formula I at which the fungicidal effect is synergistic with the multi-site inhibitors against SEPTTR in protectant applications lies within the range of about 1:272 and about 1:219. In some embodiments, the concentration ratio of the compound of Formula I at which the fungicidal effect is synergistic with chlorothalonil against SEPTTR in protectant applications is about 1:219. In some embodiments, the concentration ratio of the compound of Formula I at which the fungicidal effect is synergistic with mancozeb against SEPTTR in protectant applications is about 1:272.

The rate at which the synergistic composition is applied will depend upon the particular type of fungus to be controlled, the degree of control required and the timing and method of application. In general, the compositions described herein can be applied at an application rate of between about 40 grams per hectare (g/ha) and about 2600 g/ha based on the total amount of active ingredients in the composition.

The compositions comprising the compound of Formula I and an SBI can be applied at an application rate of between about 40 g/ha and about 600 g/ha based on the total amount of active ingredients in the composition. Epoxiconazole is applied at a rate of between about 50 g/ha and about 250 g/ha, and the compound of Formula I is applied at a rate between about 15 g/ha and about 100 g/ha. Cyproconazole is applied at a rate of between about 50 g/ha and about 250 g/ha, and the compound of Formula I is applied at a rate between about 15 g/ha and about 100 g/ha. Metconazole is applied at a rate of between about 50 g/ha and about 250 g/ha and the compound of Formula I is applied at a rate between about 15 g/ha and about 100 g/ha. Myclobutanil is applied at a rate of between about 30 g/ha and about 150 g/ha, and the compound of Formula I is applied at a rate between about 15 g/ha and about 100 g/ha. Propiconazole is applied at a rate of between about 50 g/ha and about 250 g/ha, and the compound of Formula I is applied at a rate between about 15 g/ha and about 100 g/ha. Prothioconazole is applied at a rate of between about 50 g/ha and about 250 g/ha, and the compound of Formula I is applied at a rate between about 15 g/ha and about 100 g/ha. Fluquinconazole is applied at a rate of between about 25 g/ha and about 500 g/ha, and the compound of Formula I is applied at a rate between about 15 g/ha and about 100 g/ha Difenoconazole is applied at a rate of between about 30 g/ha and about 125 g/ha, and the compound of Formula I is applied at a rate between about 15 g/ha and about 100 g/ha. Flutriafol is applied at a rate of between about 60 g/ha and about 200 g/ha, and the compound of Formula I is applied at a rate between about 15 g/ha and about 100 g/ha.

The compositions comprising the compound of Formula I and a strobilurin can be applied at an application rate of between about 65 g/ha and about 650 g/ha based on the total amount of active ingredients in the composition. Picoxystrobin is applied at a rate of between about 50 g/ha and about 250 g/ha, and the compound of Formula I is applied at a rate between about 15 g/ha and about 100 g/ha. Trifloxystrobin is applied at a rate of between about 50 g/ha and about 550 g/ha, and the compound of Formula I is applied at a rate between about 15 g/ha and about 100 g/ha. Azoxystrobin is applied at a rate of between about 100 g/ha and about 375 g/ha, and the compound of Formula I is applied at a rate between about 15 g/ha and about 100 g/ha. Fluoxastrobin is applied at a rate of between about 75 g/ha and about 200 g/ha, and the compound of Formula I is applied at a rate between about 15 g/ha and about 100 g/ha. Pyraclostrobin is applied at a rate of between about 50 g/ha and about 250 g/ha, and the compound of Formula I is applied at a rate between about 15 g/ha and about 100 g/ha. Kresoxim-methyl is applied at a rate of between about 50 g/ha and about 250 g/ha, and the compound of Formula I is applied at a rate between about 15 g/ha and about 100 g/ha.

The compositions comprising the compound of Formula I and an SDHI can be applied at an application rate of between about 40 g/ha and about 725 g/ha based on the total amount of active ingredients in the composition. Boscalid is applied at a rate of between about 100 g/ha and about 625 g/ha, and the compound of Formula I is applied at a rate between about 15 g/ha and about 100 g/ha. Isopyrazam is applied at a rate of between about 25 g/ha and about 300 g/ha, and the compound of Formula I is applied at a rate between about 15 g/ha and about 100 g/ha. Fluxapyroxad is applied at a rate of between about 45 g/ha and about 200 g/ha, and the compound of Formula I is applied at a rate between about 15 g/ha and about 100 g/ha. Penthiopyrad is applied at a rate of between about 100 g/ha and about 400 g/ha, and the compound of Formula I is applied at a rate between about 15 g/ha and about 100 g/ha Benzovindiflupyr is applied at a rate of between about 25 g/ha and about 300 g/ha, and the compound of Formula I is applied at a rate between about 15 g/ha and about 100 g/ha. Fluopyram is applied at a rate of between about 30 g/ha and about 250 g/ha, and the compound of Formula I is applied at a rate between about 15 g/ha and about 100 g/ha.

The compositions comprising the compound of Formula I and a multi-site inhibitor can be applied at an application rate of between about 1015 g/ha and about 2600 g/ha based on the total amount of active ingredients in the composition. Chlorothalonil is applied at a rate of between about 1000 g/ha and about 2500 g/ha, and the compound of Formula I is applied at a rate between about 15 g/ha and about 100 g/ha. Mancozeb is applied at a rate of between about 1500 g/ha and about 2000 g/ha, and the compound of Formula I is applied at a rate between about 15 g/ha and about 100 g/ha.

The components of the synergistic mixture described herein can be applied either separately or as part of a multipart fungicidal system.

The synergistic mixture of the present disclosure can be applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminum, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxium-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb, prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

The compositions of the present disclosure are preferably applied in the form of a formulation comprising a composition of (a) a compound of Formula I and (b) at least one fungicide selected from the group consisting of pyraclostrobin, fluoxastrobin, azoxystrobin, trifloxystrobin, picoxystrobin, kresoxim-methyl, fluxapyroxad, benzovindiflupyr, penthiopyrad, isopyrazam, boscalid, fluopyram, prothioconazole, epoxiconazole, cyproconazole, myclobutanil, metconazole, difenoconazole, propiconazole, fluquinconazole, flutriafol, mancozeb and chlorothalonil, together with a phytologically acceptable carrier.

Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of a synergistic composition.

The formulations that are applied most often are aqueous suspensions or emulsions. Either such water-soluble, water-suspendable, or emulsifiable formulations are solids, usually known as wettable powders, or liquids, usually known as emulsifiable concentrates, aqueous suspensions, or suspension concentrates. The present disclosure contemplates all vehicles by which the synergistic compositions can be formulated for delivery and use as a fungicide.

As will be readily appreciated, any material to which these synergistic compositions can be added may be used, provided they yield the desired utility without significant interference with the activity of these synergistic compositions as antifungal agents.

Wettable powders, which may be compacted to form water-dispersible granules, comprise an intimate mixture of the synergistic composition, a carrier and agriculturally acceptable surfactants. The concentration of the synergistic composition in the wettable powder is usually from about 100% to about 90% by weight, more preferably about 25% to about 75% by weight, based on the total weight of the formulation. In the preparation of wettable powder formulations, the synergistic composition can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the synergistic composition in a volatile organic solvent. Effective surfactants, comprising from about 0.5% to about 10% by weight of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the synergistic composition comprise a convenient concentration, such as from about 10% to about 50% by weight, in a suitable liquid, based on the total weight of the emulsifiable concentrate formulation. The components of the synergistic compositions, jointly or separately, are dissolved in a carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which can be employed in preparing the emulsifiable concentrates of the present disclosure are the aromatic liquids such as xylene, propyl benzene fractions, or mixed naphthalene fractions, mineral oils, substituted aromatic organic liquids such as dioctyl phthalate, kerosene, dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with the synergistic compositions. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the components of the synergistic combination either together or separately, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The synergistic composition may also be applied as a granular formulation, which is particularly useful for applications to the soil. Granular formulations usually contain from about 0.5% to about 10% by weight of the compounds, based on the total weight of the granular formulation, dispersed in a carrier which consists entirely or in large part of coarsely divided attapulgite, bentonite, diatomite, clay or a similar inexpensive substance. Such formulations are usually prepared by dissolving the synergistic composition in a suitable solvent and applying it to a granular carrier which has been preformed to the appropriate particle size, in the range of from about 0.5 to about 3 mm. Such formulations may also be prepared by making a dough or paste of the carrier and the synergistic composition, and crushing and drying to obtain the desired granular particle.

Dusts containing the synergistic composition are prepared simply by intimately mixing the synergistic composition in powdered form with a suitable dusty agricultural carrier, such as, for example, kaolin clay, ground volcanic rock, and the like. Dusts can suitably contain from about 1% to about 10% by weight of the synergistic composition/carrier combination.

The formulations may contain agriculturally acceptable adjuvant surfactants to enhance deposition, wetting and penetration of the synergistic composition onto the target crop and organism. These adjuvant surfactants may optionally be employed as a component of the formulation or as a tank mix. The amount of adjuvant surfactant will vary from 0.01 percent to 1.0 percent volume per volume (v/v) based on a spray-volume of water, preferably 0.05 to 0.5 percent. Suitable adjuvant surfactants include ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils.

The formulations may optionally include combinations that can comprise at least 1% by weight of one or more of the synergistic compositions with another pesticidal compound. Such additional pesticidal compounds may be fungicides, insecticides, nematocides, miticides, arthropodicides, bactericides or combinations thereof that are compatible with the synergistic compositions of the present disclosure in the medium selected for application, and not antagonistic to the activity of the present compounds. Accordingly, in such embodiments the other pesticidal compound is employed as a supplemental toxicant for the same or for a different pesticidal use. The pesticidal compound and the synergistic composition can generally be mixed together in a weight ratio of from 1:100 to 100:1.

The present disclosure includes within its scope methods for the control or prevention of fungal attack. These methods comprise applying to the locus of the fungus, or to a locus in which the infestation is to be prevented (for example applying to wheat or barley plants), a fungicidally effective amount of the synergistic composition. The synergistic composition is suitable for treatment of various plants at fungicidal levels, while exhibiting low phytotoxicity. The synergistic composition is useful in a protectant or eradicant fashion. The synergistic composition is applied by any of a variety of known techniques, either as the synergistic composition or as a formulation comprising the synergistic composition. For example, the synergistic compositions may be applied to the roots, seeds or foliage of plants for the control of various fungi, without damaging the commercial value of the plants. The synergistic composition is applied in the form of any of the generally used formulation types, for example, as solutions, dusts, wettable powders, flowable concentrates, or emulsifiable concentrates. These materials are conveniently applied in various known fashions.

The synergistic composition has been found to have significant fungicidal effect, particularly for agricultural use. The synergistic composition is particularly effective for use with agricultural crops and horticultural plants, or with wood, paint, leather or carpet backing.

In particular, the synergistic composition is effective in controlling a variety of undesirable fungi that infect useful plant crops. The synergistic composition may be used against a variety of Ascomycete and Basidiomycete fungi, including for example the following representative fungi species: wheat brown rust (*Puccinia triticina*; Synonym *Puccinia recondita* f. sp. *tritici*; Bayer code PUCCRT); stripe rust of wheat (*Puccinia striiformis*; Bayer code PUCCST); leaf blotch of wheat (*Mycosphaerella graminicola*; anamorph; *Septoria tritici*; Bayer code SEPTTR); glume blotch of wheat (*Leptosphaeria nodorum*; Bayer code LEPTNO; anamorph; *Stagonospora nodorum*); spot blotch of barley (*Cochliobolus sativum*; Bayer code COCHSA; anamorph; *Helminthosporium sativum*); leaf spot of sugar beets (*Cercospora beticola*; Bayer code CERCBE); leaf spot of peanut (*Mycosphaerella arachidis*; Bayer code MYCOAR; anamorph; *Cercospora arachidicola*); cucumber anthracnose (*Glomerella lagenarium*; anamorph; *Colletotrichum lagenarium*; Bayer code COLLLA) and black sigatoka disease of banana (*Mycosphaerella fijiensis*; BAYER code MYCOFI). It will be understood by those in the art that the efficacy of the synergistic compositions for one or more of the foregoing fungi establishes the general utility of the synergistic compositions as fungicides.

The synergistic compositions have a broad range of efficacy as a fungicide. The exact amount of the synergistic composition to be applied is dependent not only on the relative amounts of the components, but also on the particular action desired, the fungal species to be controlled, and the stage of growth thereof, as well as the part of the plant or other product to be contacted with the synergistic composition. Thus, formulations containing the synergistic composition may not be equally effective at similar concentrations or against the same fungal species.

The synergistic compositions are effective in use with plants in a disease-inhibiting and phytologically acceptable amount. The term "disease-inhibiting and phytologically acceptable amount" refers to an amount of the synergistic composition that kills or inhibits the plant disease for which control is desired, but is not significantly toxic to the plant. The exact concentration of synergistic composition required varies with the fungal disease to be controlled, the type of formulation employed, the method of application, the particular plant species, climate conditions, and the like.

The present compositions can be applied to fungi or their locus by the use of conventional ground sprayers, granule applicators, and by other conventional means known to those skilled in the art.

The following examples are provided for illustrative purposes and should not be construed as limitations to the disclosure.

EXAMPLES

Evaluation of Curative and Protectant Activity of Fungicide Mixtures Vs. Leaf Blotch of Wheat (*Mycosphaerella graminicola*; Anamorph; *Septoria tritici*; Bayer Code; SEPTTR);

Wheat plants (variety Yuma) were grown from seed in a greenhouse in plastic pots with a surface area of 27.5 square centimeters ($cm^2$) containing 50% mineral soil/50% soilless Metro mix, with 8-12 seedlings per pot. The plants were employed for testing when the first leaf was fully emerged, which typically took 7 to 8 days after planting. Test plants were inoculated with an aqueous spore suspension of *Septoria tritici* either 3 days prior to (3-day curative test) or 1 day after fungicide treatments (1-day protectant test). After inoculation the plants were kept in 100% relative humidity (one day in a dark dew chamber followed by two days in a lighted mist chamber) to permit spores to germinate and infect the leaf. The plants were then transferred to a greenhouse for disease to develop.

Treatments consisted of fungicide compounds pyraclostrobin, fluoxastrobin, azoxystrobin, trifloxystrobin, picoxystrobin, kresoxim-methyl, fluxapyroxad, benzovindiflupyr, penthiopyrad, isopyrazam, boscalid, fluopyram prothioconazole, epoxiconazole, cyproconazole, myclobutanil, metconazole, difenoconazole, propiconazole, fluquinconazole, flutriafol, mancozeb and chlorothalonil, either using individually or as two-way mixtures with the compound of Formula I.

Detailed dose-responses of each fungicide in 1-day protectant (1DP) and 3-day curative (3DC) SEPTTR whole plant assays were performed using high-volume spray applications, and EC) values were calculated using JMP Pro 9.0. With the exception of isopyrazam, fluxapyroxad and penthiopyrad, compounds were tested as technical grade material formulated in acetone, and spray solutions contained 10% acetone and 100 parts per million (ppm) Triton X-100. Commercially available EC formulations Seguris Flexi and Imtrex were used for isopyrazam and fluxapyroxad respectively, and the SC Fontelis for penthiopyrad. 10% EC and SC formulations of Compound I were also used to determine their $EC_{50}$ values. Compound I was mixed with each fungicide based on $EC_{50}$ values for protectant and curative activities, respectively. The EC formulation for Compound I was mixed with isopyrazam and fluxapyroxad, and the SC with penthiopyrad; the remaining mixtures involved technical materials for both Compound I and its mixing partners.

Ten milliliter (mL) fungicide solutions were applied onto 8 pots of plants using an automated booth sprayer, which utilized two 6218-1/4 JAUPM spray nozzles operating at 20 pounds per square inch (psi) set at opposing angles to cover both leaf surfaces. All sprayed plants were allowed to air dry prior to further handling. Control plants were sprayed in the same manner with the solvent blank.

When disease fully developed on the control plants, infection levels were assessed on treated plants visually and scored on a scale of 0 to 100 percent. Percentage of disease control was then calculated using the ratio of disease on treated plants relative to control plants.

Colby's equation was used to determine the fungicidal effects expected from the mixtures. (See Colby, S. R. Calculation of the synergistic and antagonistic response of herbicide combinations. *Weeds* 1967, 15, 20-22.)

The following equation was used to calculate the expected activity of mixtures containing two active ingredients, A and B:

Expected=$A+B-(A \times B/100)$

A=observed efficacy of active component A at the same concentration as used in the mixture;

B=observed efficacy of active component B at the same concentration as used in the mixture.

Representative synergistic interactions are presented in Tables 1 and 2.

TABLE 1

Synergistic Interactions of the Compound of Formula I and Other Fungicides in 1-Day Protectant (1DP) *Septoria tritici* (SEPTTR) Tests.

| Composition | Rates (ppm)* | SEPTTR* Observed* | SEPTTR* Expected* | Synergism Factor* |
|---|---|---|---|---|
| Cmpd. I + Epoxiconazole | 1.18 + 0.06 | 89 | 70 | 1.26 |
| Cmpd. I + Cyproconazole | 1.18 + 0.26 | 91 | 81 | 1.13 |
| Cmpd. I + Metconazole | 1.18 + 0.04 | 86 | 71 | 1.21 |
| Cmpd. I + Myclobutanil | 1.18 + 4.81 | 95 | 70 | 1.35 |
| Cmpd. I + Propiconazole | 1.18 + 0.04 | 96 | 67 | 1.43 |
| Cmpd. I + Prothioconazole | 1.18 + 0.64 | 90 | 70 | 1.29 |
| Cmpd. I + Picoxystrobin | 1.18 + 3.08 | 85 | 75 | 1.14 |
| Cmpd. I + Trifloxystrobin | 1.18 + 0.3 | 84 | 73 | 1.15 |
| Cmpd. I + Azoxystrobin | 1.18 + 0.64 | 94 | 67 | 1.39 |
| Cmpd. I + Fluoxastrobin | 1.18 + 0.17 | 89 | 74 | 1.20 |
| Cmpd. I + Boscalid | 1.18 + 1.56 | 79 | 67 | 1.18 |
| Cmpd. $I^a$ + Isopyrazam | 8.41 + 10.9 | 100 | 91 | 1.10 |
| Cmpd. $I^a$ + Fluxapyroxad | 8.41 + 1.92 | 100 | 42 | 2.41 |
| Cmpd. $I^b$ + Penthiopyrad | 2.56 + 4.98 | 100 | 59 | 1.68 |
| Cmpd. I + Benzovindiflupyr | 1.18 + 0.15 | 49 | 32 | 1.50 |
| Cmpd. I + Fluquinconazole | 1.18 + 0.007 | 39 | 31 | 1.25 |
| Cmpd. I + Difenoconazole | 1.18 + 0.0015 | 46 | 33 | 1.38 |
| Cmpd. I + Pyraclostrobin | 1.18 + 0.028 | 46 | 40 | 1.16 |
| Cmpd. I + Fluopyram | 1.18 + 4.19 | 43 | 34 | 1.26 |
| Cmpd. I + Flutriafol | 1.18 + 0.23 | 30 | 27 | 1.10 |
| Cmpd. I + Kresoxim-methyl | 1.18 + 25 | 51 | 35 | 1.45 |
| Cmpd. I + Chlorothalonil | 1.18 + 258 | 41 | 31 | 1.30 |
| Cmpd. I + Mancozeb | 1.18 + 321 | 42 | 31 | 1.34 |

*SEPTTR = Leaf Blotch of Wheat; *Septoria tritici*
*DC Observed = Observed disease control at the test rates
*DC Expected = Disease control expected as predicted by the Colby equation
*ppm = Parts per million
*Synergism factor = % DC Observed/% DC Expected
*Cmpd $I^a$ = An EC formulation of compound I was used
*Cmpd $I^b$ = An SC formulation of compound I was used

TABLE 2

Synergistic Interactions of the Compound of Formula I and Other Fungicides in 3-Day Curative (3DC) *Septoria tritici* (SEPTTR) Tests.

| Composition | Rates (ppm)* | SEPTTR* Observed* | SEPTTR* Expected* | Synergism Factor* |
|---|---|---|---|---|
| Cmpd. I + Epoxiconazole | 0.18 + 0.05 | 99 | 77 | 1.29 |
| Cmpd. I + Cyproconazole | 0.18 + 0.54 | 98 | 84 | 1.17 |
| Cmpd. I + Metconazole | 0.18 + 0.08 | 93 | 67 | 1.38 |
| Cmpd. I + Myclobutanil | 0.18 + 4.86 | 94 | 62 | 1.51 |
| Cmpd. I + Propiconazole | 0.18 + 0.38 | 77 | 52 | 1.48 |
| Cmpd. I + Prothioconazole | 0.18 + 3.89 | 58 | 50 | 1.18 |
| Cmpd. I + Picoxystrobin | 0.18 + 5.4 | 68 | 92 | 0.73 |
| Cmpd. I + Trifloxystrobin | 0.18 + 1.74 | 69 | 95 | 0.73 |
| Cmpd. I + Azoxystrobin | 0.18 + 0.83 | 61 | 79 | 0.77 |
| Cmpd. I + Fluoxastrobin | 0.18 + 0.29 | 51 | 78 | 0.65 |
| Cmpd. I + Boscalid | 0.18 + 2.37 | 43 | 93 | 0.46 |
| Cmpd. $I^a$ + Isopyrazam | 2.27 + 2.19 | 74 | 64 | 1.15 |
| Cmpd. $I^a$ + Fluxapyroxad | 2.27 + 0.36 | 71 | 53 | 1.33 |
| Cmpd. $I^b$ + Penthiopyrad | 0.2 + 0.86 | 77 | 61 | 1.25 |
| Cmpd. I + Benzovindiflupyr | 0.18 + 0.54 | 72 | 56 | 1.29 |
| Cmpd. I + Fluquinconazole | 0.18 + 0.24 | 27 | 64 | 0.42 |
| Cmpd. I + Difenoconazole | 0.18 + 0.0015 | 21 | 62 | 0.33 |
| Cmpd. I + Pyraclostrobin | 0.18 + 0.009 | 71 | 59 | 1.20 |
| Cmpd. I + Fluopyram | 0.18 + 4.96 | 78 | 51 | 1.54 |

TABLE 2-continued

Synergistic Interactions of the Compound of Formula I and Other
Fungicides in 3-Day Curative (3DC) *Septoria tritici* (SEPTTR) Tests.

| Composition | Rates (ppm)* | SEPTTR* Observed* | Expected* | Synergism Factor* |
|---|---|---|---|---|
| Cmpd. I + Flutriafol | 0.18 + 3.7 | 81 | 64 | 1.27 |
| Cmpd. I + Kresoxim-methyl | 0.18 + 45 | 23 | 42 | 0.54 |

*SEPTTR = Leaf Blotch of Wheat; *Septoria tritici*
*DC Observed = Observed disease control at the test rates
*DC Expected = Disease control expected as predicted by the Colby equation
*ppm = Parts per million
*Synergism factor = % DC Observed/% DC Expected
*Cmpd I$^a$ = An EC formulation of compound I was used
*Cmpd I$^b$ = An SC formulation of compound I was used

What is claimed is:

1. A synergistic fungicidal mixture comprising at least one fungicidal multi-site inhibitor selected from the group consisting of captan, chlorothalonil, copper bis(3-phenylsalicylate), copper hydroxide, copper octanoate, copper oxychloride, copper sulfate, copper sulfate (tribasic), copper zinc chromate, cupric hydrazinium sulfate, cuprobam, cuprous oxide, folpet, mancozeb, maneb, metiram, propineb, mancopper and oxine-copper and a fungicidally effective amount of a compound of Formula I:

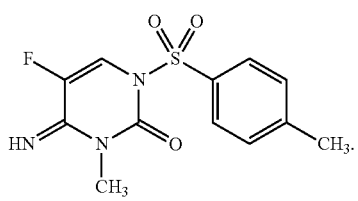

Formula I

2. The synergistic fungicidal mixture of claim 1, wherein the at least one fungicidal multi-site inhibitor is selected from the group consisting of copper bis(3-phenylsalicylate), copper hydroxide, copper octanoate, copper oxychloride, copper sulfate, copper sulfate (tribasic), copper zinc chromate, cupric hydrazinium sulfate, cuprobam, cuprous oxide, mancopper and oxine-copper.

3. The synergistic fungicidal mixture of claim 1, wherein the at least one fungicidal multi-site inhibitor is captan.

4. The synergistic fungicidal mixture of claim 1, wherein the at least one fungicidal multi-site inhibitor is maneb.

5. The synergistic fungicidal mixture of claim 1, wherein the at least one fungicidal multi-site inhibitor is metiram.

6. The synergistic fungicidal mixture of claim 1, wherein the at least one fungicidal multi-site inhibitor is propineb.

7. The synergistic fungicidal mixture of claim 1, wherein the concentration of the compound of Formula I to the fungicidal multi-site inhibitor is from 1:250 to 787:1.

8. The synergistic fungicidal mixture of claim 1, wherein the mixture is a tank mix.

9. A synergistic fungicidal composition comprising an agriculturally acceptable adjuvant or carrier and a fungicidally effective amount of the synergistic fungicidal mixture of claim 1.

10. A method for the prevention or control of a fungal pathogen attack on a plant, wherein the method comprises applying a fungicidally effective amount of the synergistic fungicidal mixture of claim 1:

(i) to a locus of the fungus;
(ii) to a locus in which fungal infestation is to be prevented or controlled; and/or
(iii) to the plant.

11. A synergistic fungicidal mixture comprising at least one strobilurin fungicide selected from the group consisting of azoxystrobin, dimoxystrobin, fluoxastrobin, kresoxim-methyl, orysastrobin, picoxystrobin, pyraclostrobin and trifloxystrobin and a fungicidally effective amount of a compound of Formula I:

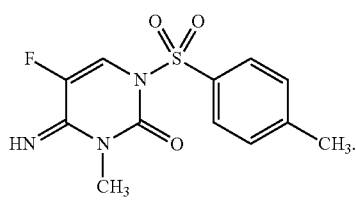

Formula I

12. The synergistic fungicidal mixture of claim 11, wherein the at least one strobilurin fungicide is selected from the group consisting of dimoxystrobin and orysastrobin.

13. The synergistic fungicidal mixture of claim 11, wherein the at least one strobilurin fungicide is fluoxastrobin.

14. The synergistic fungicidal mixture of claim 11, wherein the at least one strobilurin fungicide is kresoxim-methyl.

15. The synergistic fungicidal mixture of claim 11, wherein the at least one strobilurin fungicide is picoxystrobin.

16. The synergistic fungicidal mixture of claim 11, wherein the at least one strobilurin fungicide is trifloxystrobin.

17. The synergistic fungicidal mixture of claim 11, wherein the concentration of the compound of Formula I to the strobilurin fungicide is from 1:250 to 787:1.

18. The synergistic fungicidal mixture of claim 11, wherein the mixture is a tank mix.

19. A synergistic fungicidal composition comprising an agriculturally acceptable adjuvant or carrier and a fungicidally effective amount of the synergistic fungicidal mixture of claim 11.

20. A method for the prevention or control of a fungal pathogen attack on a plant, wherein the method comprises applying a fungicidally effective amount of the synergistic fungicidal mixture of claim 11:
- (i) to a locus of the fungus;
- (ii) to a locus in which fungal infestation is to be prevented or controlled; and/or
- (iii) to the plant.

* * * * *